(12) United States Patent
Lee et al.

(10) Patent No.: US 11,937,971 B2
(45) Date of Patent: Mar. 26, 2024

(54) METHOD FOR CLASSIFYING DISEASE USING ARTIFICIAL INTELLIGENCE AND ELECTRONIC APPARATUS THEREFOR

(71) Applicant: SMARTSOUND CORPORATION, Seoul (KR)

(72) Inventors: Jung Ho Lee, Seoul (KR); Won Yang Cho, Gyeonggi-do (KR); Eun Joo Lee, Seoul (KR)

(73) Assignee: SMARTSOUND CORPORATION, Seoul (KR)

( * ) Notice: Subject to any disclaimer, the term of this patent is extended or adjusted under 35 U.S.C. 154(b) by 0 days.

(21) Appl. No.: 18/143,919

(22) Filed: May 5, 2023

(65) Prior Publication Data

US 2024/0023922 A1    Jan. 25, 2024

(30) Foreign Application Priority Data

Jul. 22, 2022   (KR) ......................... 10-2022-0090887

(51) Int. Cl.
*A61B 7/00* (2006.01)
*A61B 5/00* (2006.01)
*G16H 10/60* (2018.01)

(52) U.S. Cl.
CPC ............ *A61B 7/003* (2013.01); *A61B 5/7267* (2013.01); *G16H 10/60* (2018.01)

(58) Field of Classification Search
None
See application file for complete search history.

(56) References Cited

U.S. PATENT DOCUMENTS

| | | | | |
|---|---|---|---|---|
| D769,278 S * | 10/2016 | Ukrainsky | ............... | D14/486 |
| 11,284,827 B2 * | 3/2022 | Telenkov | ............... | A61B 7/04 |
| 11,550,276 B1 * | 1/2023 | Lee | ............... | G06F 18/214 |
| 2008/0082017 A1 | 4/2008 | Savic | | |
| 2018/0132815 A1 * | 5/2018 | Tsai | ............... | A61B 5/42 |
| 2020/0046244 A1 * | 2/2020 | Alam | ............... | G06N 3/045 |
| 2020/0146623 A1 | 5/2020 | Anushiravani et al. | | |

FOREIGN PATENT DOCUMENTS

| | | |
|---|---|---|
| CN | 112908291 A | 6/2021 |
| JP | H03-503962 A | 9/1991 |
| JP | 2021-502222 A | 1/2021 |
| JP | 2021-133005 A | 9/2021 |
| JP | 2021-524958 A | 9/2021 |
| KR | 10-2011-0127785 A | 11/2011 |
| KR | 10-2017-0064960 A | 6/2017 |
| WO | 2013/089072 A1 | 6/2013 |

OTHER PUBLICATIONS

Japanese Office Action dated 2023-10-17 corresponding to application No. 2023-119199.

* cited by examiner

*Primary Examiner* — Michael R Bloch

(74) *Attorney, Agent, or Firm* — Nath, Goldberg & Meyer; Jerald L. Meyer

(57) ABSTRACT

Provided is a method for classifying diseases using artificial intelligence (AI) of an electronic apparatus. The method for classifying diseases may comprise obtaining auscultation sound data and auscultation position data, obtaining feature information based on the auscultation sound data and obtaining auscultation position information based on the auscultation position data, generating combined information by combining the feature information and the auscultation position information, and identifying at least one of disease information corresponding to the combined information, by using an AI model.

18 Claims, 36 Drawing Sheets

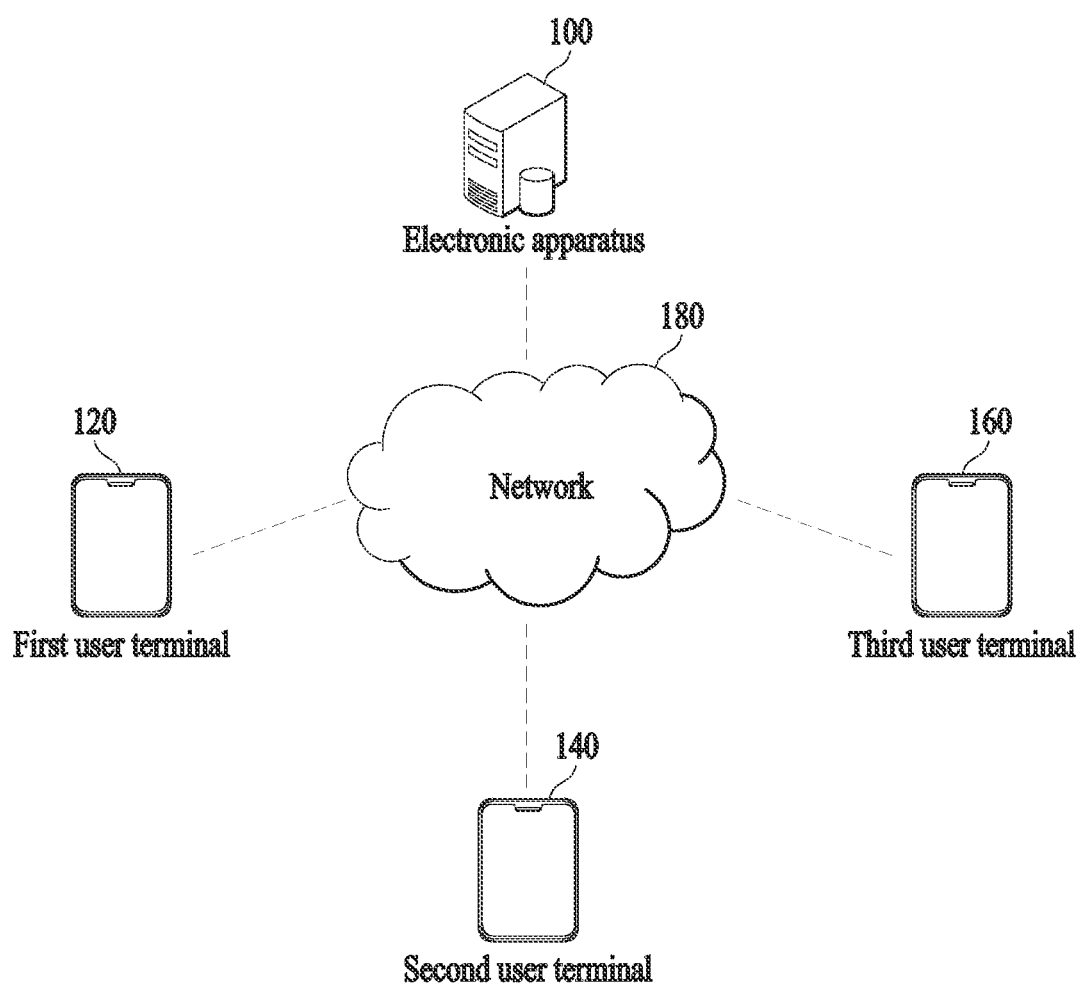

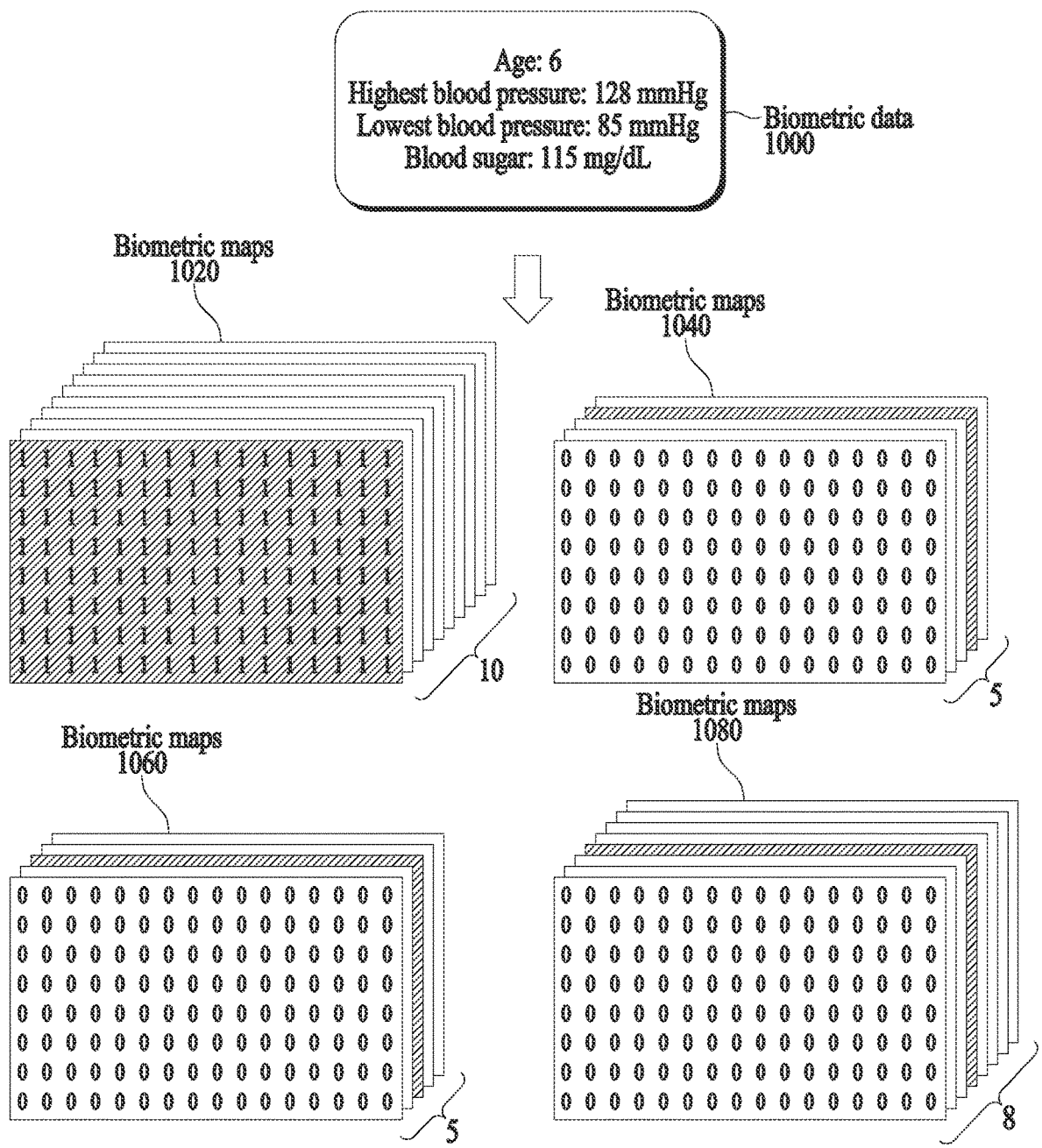

METHOD FOR CLASSIFYING DISEASE USING ARTIFICIAL INTELLIGENCE AND ELECTRONIC APPARATUS THEREFOR

CROSS-REFERENCE TO RELATED APPLICATION(S)

This application claims the benefit of Korean Patent Application No. 10-2022-0090887, filed on Jul. 22, 2022, in the Korean Intellectual Property Office, the disclosure of which is incorporated herein by reference.

BACKGROUND

1. Field of the Invention

Example embodiments relate to an electronic apparatus for training an artificial intelligence (AI) model based on training data including auscultation sound data and auscultation position data and for classifying diseases more accurately using the trained AI model, and a method for controlling the same.

2. Description of the Related Art

As the use of the Internet becomes common and the lifespan of the population increases, interest in the home healthcare market is increasing. Home healthcare refers to a service in which a user receives medical care, treatment and support remotely from the user's home without visiting a hospital.

Specifically, in the limelight is a service that measures the auscultation sound of the body parts of the heart, lungs and intestines using a product such as a smart stethoscope, provides information on the presence or absence of disease based on the measured auscultation sound, and diagnoses the disease. However, since current technology provides disease diagnosis services based only on auscultation sound data, there are limitations in the accuracy of disease diagnosis.

SUMMARY

An aspect provides a method for classifying diseases using AI, and an electronic apparatus using the same. More specifically, provided is an electronic apparatus for training an AI model based on training data including auscultation sound data and auscultation position data and classifying diseases more accurately using the trained AI model, and a method for controlling the same.

However, the goals to be achieved by example embodiments of the present disclosure are not limited to the technical aspects described above, and other goals may be inferred from the following example embodiments.

According to an aspect, there is provided a method for classifying diseases using AI of an electronic apparatus, the method including obtaining auscultation sound data and auscultation position data, obtaining feature information based on the auscultation sound data and obtaining auscultation position information based on the auscultation position data, generating combined information by combining the feature information and the auscultation position information, and identifying at least one of disease information corresponding to the combined information, by using an AI model.

According to an example embodiment, the method may further comprise obtaining biometric data and obtaining biometric information based on the biometric data, wherein the combined information may be further combined with the biometric information.

According to an example embodiment, the biometric data may include at least one of heart beat regularity data, respiration rate data, respiratory regularity data, body temperature data, age data, blood pressure data, and blood sugar data.

According to an example embodiment, the feature information and the auscultation position information may have a vector form, and the generating the combined information may comprise generating the combined information by concatenating the feature information and the auscultation position information.

According to an example embodiment, the auscultation position information may include one or more components corresponding to possible auscultation positions, and from among the one or more components corresponding to the possible auscultation positions, a component corresponding to the auscultation position may have a first value and other remaining components have a second value.

According to an example embodiment, the method may further comprise obtaining biometric data and obtaining biometric information in a vector form based on the biometric data, wherein the combined information may be further concatenated with the biometric information.

According to an example embodiment, the biometric information may include one or more components corresponding to a set number of categories, and among the one or more components corresponding to the set number of categories, a component corresponding to a category including a value of the biometric data may have a first value and other remaining components have a second value.

According to an example embodiment, the feature information and the auscultation position information may have a form of a map, and the generating the combined information may comprise generating the combined information by adding the auscultation position information as a channel to the feature information.

According to an example embodiment, the auscultation position information may include one or more maps corresponding to possible auscultation positions, and from among the one or more maps corresponding to the possible auscultation positions, a component of a map corresponding to the auscultation position may have a first value and components of other remaining maps have a second value.

According to an example embodiment, the method may further comprise obtaining biometric data and obtaining biometric information in a form of a map based on the biometric data, wherein biometric information may be further added to the combined information as a channel.

According to an example embodiment, the biometric information may include one or more maps corresponding to a set number of categories, and among the one or more maps corresponding to the set number of categories, a component of a map corresponding to a category including a value of the biometric data may have a first value and components of other remaining maps have a second value.

According to an example embodiment, the auscultation sound data may include at least one of heart sound data and lung sound data, and the auscultation position data may include data related to an auscultation position for a heart sound and data related to an auscultation position for a lung sound.

According to an example embodiment, the auscultation sound data may include heart sound data, the AI model may include a first AI model for classifying heart-related diseases, the obtaining the feature information may comprise removing a frequency domain other than a frequency domain in which a heart sound is present from the auscultation sound data, and the identifying at least one of disease information may comprise identifying at least one of disease information about a heart corresponding to the combined information using the first AI model.

According to an example embodiment, the auscultation sound data may include lung sound data, the AI model may include a second AI model for classifying lung-related diseases, the obtaining the feature information may comprise removing a frequency domain other than a frequency domain in which a lung sound is present from the auscultation sound data, and the identifying at least one of disease information may comprise identifying at least one of disease information about a lung corresponding to the combined information using the second AI model.

According to an example embodiment, the obtaining the auscultation position data may comprise obtaining medical record data and obtaining the auscultation position data from the medical record data using an AI model that extracts a keyword.

According to an example embodiment, the AI model may be trained based on a training dataset including one or more auscultation sound data, one or more auscultation position data and one or more disease data.

According to an example embodiment, the training dataset further may include one or more biometric data.

According to an example embodiment, the AI model may include a first AI model for classifying heart-related diseases and a second AI model for classifying lung-related diseases, the first AI model may be trained based on a training dataset including one or more heart sound data, one or more auscultation position data of heart sound and one or more heart disease data, and the second AI model may be trained based on a training dataset including one or more lung sound data, one or more auscultation position data of lung sound and one or more lung disease data.

According to another aspect, there is provided an electronic apparatus, including a communication apparatus, a memory and a controller, wherein the controller is configured to obtain auscultation sound data and auscultation position data, obtain feature information based on the auscultation sound data and obtaining auscultation position information based on the auscultation position data, generate combined information by combining the feature information and the auscultation position information, and identify at least one of disease information corresponding to the combined information, by using an AI model.

According to another aspect, there is provided a computer-readable non-transitory recording medium having a program for executing a method performed by the electronic apparatus on a computer.

Additional aspects of example embodiments will be set forth in part in the description which follows and, in part, will be apparent from the description, or may be learned by practice of the disclosure.

According to example embodiments, by using an AI model trained based on auscultation position data as well as auscultation sound data, when the auscultation sound data and the auscultation position data are input, it is possible to determine with higher accuracy whether or not a user has a disease and/or what disease the user has.

Further, according to example embodiments, by using an AI model trained based on auscultation position data and biometric data as well as auscultation sound data, when the auscultation sound data, the auscultation position data and the biometric data are input, it is possible to determine with higher accuracy whether or not a user has a disease and/or what disease the user has.

Further, according to example embodiments, by using an AI model trained based on different training data depending on the body part or species that the user wishes to diagnose, when auscultation sound data and auscultation position data are input, it is possible to determine with higher accuracy whether or not a user or species has a disease and/or what disease the user or species has.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

BRIEF DESCRIPTION OF THE DRAWINGS

These and/or other aspects, features, and advantages of the invention will become apparent and more readily appreciated from the following description of example embodiments, taken in conjunction with the accompanying drawings of which:

FIG. 1 illustrates a system according to an example embodiment;

FIG. 10 is a diagram for explaining a process in which an electronic apparatus obtains biometric maps based on biometric data according to an example embodiment;

DETAILED DESCRIPTION

Figure 2A:
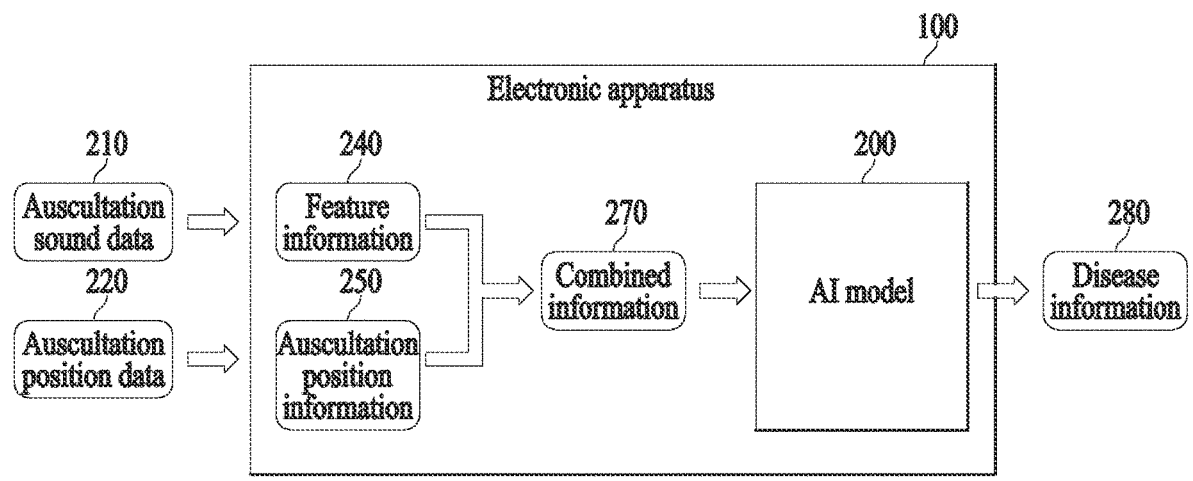
FIGS. 2A to 2C are diagrams for explaining a process of classifying a disease by an electronic apparatus according to an example embodiment.

Terms used in the example embodiments are selected from currently widely used general terms when possible while considering the functions in the present disclosure. However, the terms may vary depending on the intention or precedent of a person skilled in the art, the emergence of new technology, and the like. Further, in certain cases, there are also terms arbitrarily selected by the applicant, and in the cases, the meaning will be described in detail in the corresponding descriptions. Therefore, the terms used in the present disclosure should be defined based on the meaning of the terms and the contents of the present disclosure, rather than the simple names of the terms.

Throughout the specification, when a part is described as "comprising or including" a component, it does not exclude another component but may further include another component unless otherwise stated.

Expression "at least one of a, b and c" described throughout the specification may include "a alone," "b alone," "c alone," "a and b," "a and c," "b and c" or "all of a, b and c."

In the present disclosure, a "terminal" may be implemented as, for example, a computer or a portable terminal capable of accessing a server or another terminal through a network. Here, the computer may include, for example, a notebook, a desktop computer, and/or a laptop computer which are equipped with a web browser. The portable terminal may be a wireless communication apparatus ensuring portability and mobility, and include (but is not limited to) any type of handheld wireless communication apparatus, for example, a tablet PC, a smartphone, a communication-based terminal such as international mobile telecommunication (IMT), code division multiple access (CDMA), W-code division multiple access (W-CDMA), long term evolution (LTE), or the like.

Hereinafter, example embodiments of the present disclosure will be described in detail with reference to the accompanying drawings so that those of ordinary skill in the art to which the present disclosure pertains may easily implement them. However, the present disclosure may be implemented in multiple different forms and is not limited to the example embodiments described herein.

Functions related to AI according to the present disclosure are operated through a processor and a memory. A processor may consist of one or a plurality of processors. Here, the one or more processors may be a general-purpose processor such as a central processing unit (CPU), an arithmetic processor (AP) and a digital signal processor (DSP), a graphics-only processor such as a graphics processing unit (GPU) and a vision processing unit (VPU) and/or an AI-dedicated processor such as a neural processing unit (NPU). One or more processors control input data to be processed according to predefined operating rules or AI models stored in a memory. Alternatively, if the one or more processors are AI-dedicated processors, the AI-dedicated processors may be designed with a hardware structure specialized for the processing of a specific AI model.

Predefined action rules or AI models are characterized by being created through AI learning. Here, "being created through AI learning" indicates that a basic AI model is learned using training data by a learning algorithm, so that a predefined action rule or AI model that is set to perform a desired feature (or a goal) is generated. The AI learning may be performed in an apparatus itself in which AI according to the present disclosure is performed, or may be performed through a separate server and/or system. Examples of learning algorithms include supervised learning, unsupervised learning, semi-supervised learning or reinforcement learning, but the present disclosure is not limited thereto.

The AI model may be configured to have a plurality of neural network layers. Each of the plurality of neural network layers has a plurality of weight values, and neural network calculation is performed through calculation between the calculation result of the previous layers and multiple weight values. The plurality of weight values of the plurality of neural network layers may be optimized by the learning result of the AI model. For example, during the learning process, a plurality of weight values may be updated so that the loss value or cost value obtained from the AI model is reduced or minimized. Artificial neural networks may include deep neural network (DNN), convolutional neural network (CNN), recurrent neural network (RNN), restricted Boltzmann machine (RBM), deep belief network (DBN), bidirectional recurrent deep neural network (BRDNN) and Deep Q-Networks. However, the present disclosure is not limited thereto.

In the present disclosure, an operation classifying a disease may indicate an operation of determining whether an auscultated user has a disease or an operation of determining what a disease the user has, and may be mixed with an operation of diagnosing a disease. However, the present disclosure is not limited thereto.

Hereinafter, example embodiments of the present disclosure will be described in detail with reference to the drawings.

FIG. 1 illustrates a system according to an example embodiment.

Referring to FIG. 1, the system may include at least one of an electronic apparatus 100, one or more user terminals 120, 140 and 160, and a network 180. Meanwhile, in the system illustrated in FIG. 1, only elements related to the example embodiments are illustrated. Therefore, those skilled in the art can understand that other general-purpose elements may be further included in addition to the elements illustrated in FIG. 1.

The electronic apparatus 100 is an apparatus that constitutes and provides various types of information. The electronic apparatus 100 may obtain auscultation sound data and auscultation position data, and may identify disease information corresponding to the auscultation sound data and the auscultation position data using an AI model. After then, the electronic apparatus 100 may provide the identified disease information through a web page or an application screen, or provide in a form that can be displayed on a web page or an application screen in a terminal that receives the information.

One or more user terminals 120, 140 and 160 are terminals used by each user, and the users may access services provided by the network 180 using their respective user terminals 120, 140 and 160. For example, the electronic apparatus 100 may provide an application for diagnosing a user's disease to one or more user terminals 120, 140 and 160, and users may measure an auscultation sound by using the application installed in their respective user terminals 120, 140 and 160, and receive disease diagnosis results accordingly.

One or more user terminals 120, 140 and 160, and the electronic apparatus 100 may communicate with each other within the network 180. The network 180 includes a local area network (LAN), a wide area network (WAN), a value added network (VAN), a mobile radio communication network, a satellite communication network, and combination thereof. The network is a data communication network in a comprehensive sense that enables each network constituent entity shown in FIG. 1 to communicate smoothly with each other, and may include a wired Internet, a wireless Internet, and a mobile wireless communication network. Wireless communication is, for example, wireless LAN (Wi-Fi), Bluetooth, Bluetooth low energy, ZigBee, WFD (Wi-Fi Direct), ultra wideband (UWB), infrared data association (IrDA), and near field communication (NFC), etc., but it is not limited thereto.

Figure 2B:
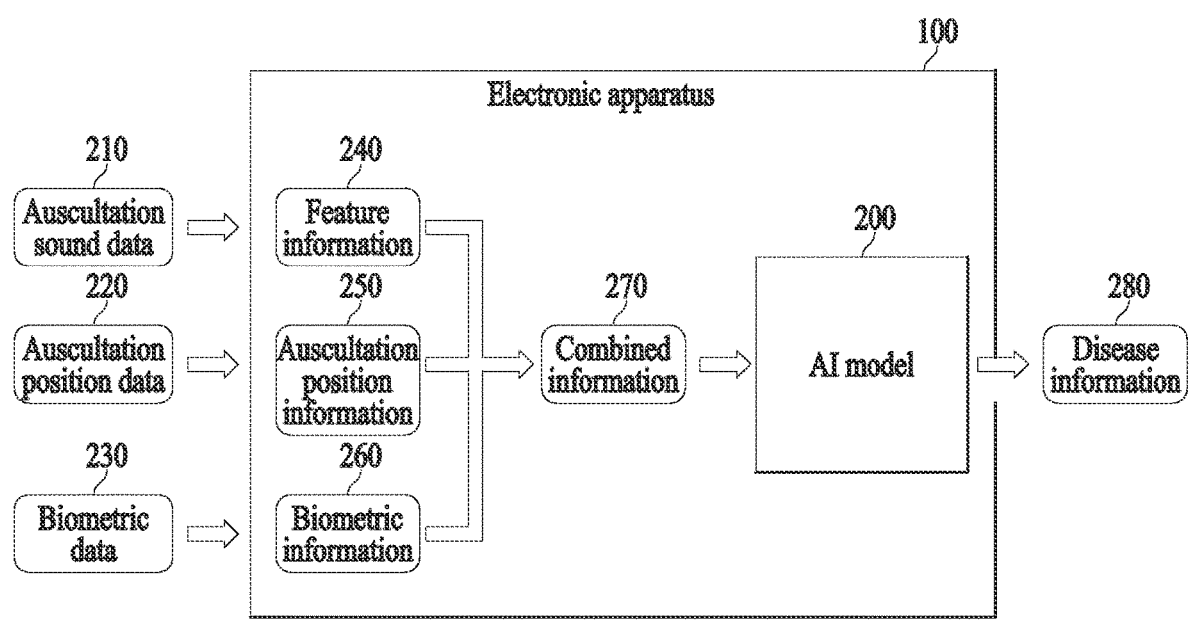
Figure 2C:
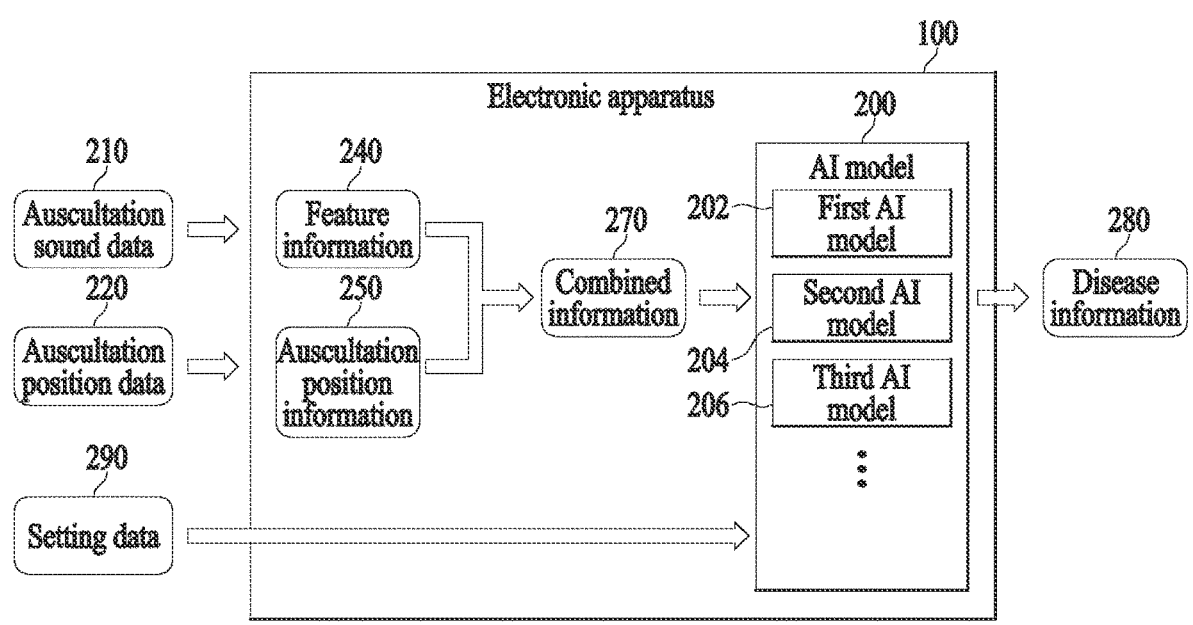

FIGS. 2A to 2C are diagrams for explaining a process of classifying a disease by the electronic apparatus 100 according to an example embodiment. Here, a rounded rectangle represents data or information.

Referring to FIG. 2A, the electronic apparatus 110 may obtain auscultation sound data 210 and auscultation position data 220 according to the example embodiment. For example, a user may measure an auscultation sound by placing a smart stethoscope on the body part to be diagnosed, and a user terminal may transmit the auscultation sound data 210 obtained from the smart stethoscope to the electronic apparatus 100. Further, the user terminal may identify an auscultation position through sensors of the smart stethoscope used when the user measured the auscultation sound, obtain a user input for directly selecting an auscultation position from among positions where an auscultation can be performed that are displayed on the display of the user terminal, and transmit the obtained auscultation position data 220 to the electronic apparatus 100.

According to an example embodiment, the electronic apparatus 100 may obtain feature information 240 based on the auscultation sound data 210. For example, the electronic apparatus 100 convert the obtained auscultation sound data 210 into a spectrogram image, and then obtain the feature information 240 in the form of a feature vector or feature map using a CNN model, a temporary CNN (TCNN) model, or a CNN-long short term memory (CNN-LSTM) model. Here, a spectrogram indicates a tool for visualizing sound or waves by expressing the difference in amplitude according to changes in the time axis and frequency axis as a difference in print density or display color.

According to an example embodiment, the electronic apparatus 100 may obtain auscultation position information 250 based on the auscultation position data 220. For example, the electronic apparatus 100 may obtain the auscultation position information 250 in a vector form by embedding the auscultation position data 220. With regard thereto, it will be described in detail with reference to FIGS. 5A to 5F, and FIGS. 6A and 6B. Alternatively, the electronic apparatus 100 may obtain the auscultation position information 250 in the form of a map from the auscultation position data 220. With regard thereto, it will be described in detail with reference to FIGS. 8A to 8F and FIGS. 9A to 9C.

According to an example embodiment, the electronic apparatus 100 may generate combined information 270 by combining the feature information 240 and the auscultation position information 250. For example, the electronic apparatus 100 may generate the combined information 270 by concatenating the feature information 240 and the auscultation position information 250. With regard thereto, it will be described in detail with reference to FIGS. 3A to 3D. Alternatively, the electronic apparatus 100 may generate the combined information 270 by adding the auscultation position information 250 as a channel to the feature information 240. With regard thereto, it will be described with reference to FIGS. 4A to 4D.

According to an example embodiment, the electronic apparatus 100 may identify at least one of disease information 280 corresponding to the combined information 270, using an AI model 200. For example, the electronic apparatus 100 may input the generated the combined information 270 to the AI model 200, and may identify at least one of disease information 280 that is output from the AI model 200.

Here, the AI model 200 is trained based on the auscultation sound data, auscultation position data and disease data. The AI model 200 may output the disease information 280 based on the combined information 270 obtained from the auscultation sound data 210 and the auscultation position data 220, thereby classifying a disease with higher accuracy. For example, the AI model 200 may be trained based on auscultation sound data at an aortic valve position of a patient with aortic stenosis (AS). Accordingly, when auscultation sound data and aortic valve position data at the aortic valve position are entered, the AI model may determine with higher accuracy whether the user of the input data has the AS. Further, the AI model 200 may be trained based on auscultation sound data at various positions including a pulmonic valve, a tricuspid valve, and a mitral valve or bicuspid valve, as well as the auscultation sound data at the aortic valve position of the patient with the AS. Accordingly, the AI model may determine whether the user of the input data has the AS even when auscultation sound data and corresponding position data are input at a position other than the aortic valve positon.

According to an example embodiment, the AI model 200 may output one or more pieces of disease information. For example, the AI model 200 may output a disease with the highest probability corresponding to the auscultation sound measured by the user, or may output a plurality of diseases corresponding to the auscultation sound measured by the user.

According to an example embodiment, the electronic apparatus 100 may display the identified disease information on a display of the electronic apparatus 100 or transmit it to a user terminal. Based on the received disease information 280, if there is something wrong with the auscultation sound, the user terminal may provide the user with whether the body part where the auscultation sound is measured with the smart stethoscope is normal and/or provide the user with information about what kind of disease is expected.

Referring to FIG. 2B, the electronic apparatus 100 may obtain the auscultation sound data 210, the auscultation position data 220 and biometric data 230 according to the example embodiment. For example, the user may measure the biometric data 230 including heartbeat regularity, respiratory rate, respiratory regularity, body temperature, age, blood pressure and blood sugar, by using the user terminal or the user may directly input the biometric data 230, and the user terminal may transmit the obtained biometric data 230 to the electronic apparatus 100.

Here, among the data included in the biometric data, the regularity of the measured target may indicate a ratio of the number of times the measured target is identified for each set period of time based on the number of times the measured target is identified during the set period of time. For example, if the user's heart rate is identified as five times for 10 seconds, and the user's hear rate is identified four times for 10 seconds later, the user's heart beat regularity may be 80%. Alternatively, if the user's heart rate is identified to be 15 times for one minute, and if the user's heart rate is identified to be 18 times for one minute later, the user's respiratory regularity may be 120%.

According to an example embodiment, the electronic apparatus 100 may obtain the feature information 240 based on the auscultation sound data 210, obtain the auscultation position information 250 based on the auscultation position data 220, and obtain biometric information 260 based on the biometric data 230. For example, the electronic apparatus 100 may obtain the biometric information 260 in a vector form by embedding the biometric data 230. With regard thereto, it will be described in detail with reference to FIG. 7. Alternatively, the electronic apparatus 100 may obtain the map-type biometric information 260 from the biometric data 230. With regard thereto, it will be described in detail with reference to FIG. 10.

According to an example embodiment, the electronic apparatus 100 may generate the combined information 270 by combining the feature information 240, the auscultation position information 250 and the biometric information 260. For example, the electronic apparatus 100 may generate the combined information 270 by concatenating the feature information 240, the auscultation position information 250 and the biometric information 260. With regard thereto, it will be described in detail with reference to FIGS. 3A to 3D. Alternatively, the electronic apparatus 100 may generate the combined information 270 by adding the auscultation position information 250 and the biometric information 260 to the feature information 240 as channels. With regard thereto, it will be described in detail with reference to FIGS. 4A to 4D.

According to an example embodiment, the electronic apparatus 100 may identify at least one of disease information 280 corresponding to the combined information 270, using the AI model 200. For example, the electronic apparatus 100 may input the generated combined information 270 to the AI model 200 and identify at least one of disease information 280 that is output from the AI model 200.

Here, the AI model 200 is trained based on auscultation sound data, auscultation position data, biometric data and disease data. The AI model 200 may output the disease information 280 based on the combined information 270 obtained from the auscultation sound data 210, the auscultation position data 220 and the biometric data 230, thereby classifying a disease with higher accuracy. For example, in the case of diagnosis of a disease related to the heart, the electronic apparatus 100 may train the AI model 200 by using heart beat regularity data together with heart sound data and auscultation position data of heart sound, and input heart sound data, auscultation position data of heart sound and heart beat regularity data to the AI, thereby classifying cardiac diseases with higher accuracy. Alternatively, in the case of diagnosis of diseases related to the lungs, the electronic apparatus 100 may train the AI model 200 using respiration rate data/respiratory regularity data together with lung sound data and auscultation position data of lung sound, and input lung sound data, auscultation position data of lung sound and respiration rate data/respiratory regularity data to the AI model 200, thereby classifying lung-related diseases with higher accuracy. In the case of disease diagnosis related to animals, the electronic apparatus 100 may train the AI model 200 using respiratory regularity data and body temperature data together with auscultation sound data and auscultation position data, and input auscultation sound data, auscultation position data, respiratory regularity data and body temperature data into the AI model 200, thereby classifying diseases related to animals with higher accuracy.

Referring to FIG. 2C, the electronic apparatus 100 may obtain the auscultation sound data 210, the auscultation position data 220 and setting data 290 according to the example embodiment. For example, a user may input a set value related to which body part, such as the heart, lungs, or intestines, to be diagnosed with a disease or whether to diagnose an animal, into the user terminal, and the user terminal may transmit the obtained setting data 290 to the electronic apparatus 100.

According to an example embodiment, the electronic apparatus 100 may obtain the feature information 240 based on the auscultation sound data 210 and the setting data 290. More specifically, the electronic apparatus 100 may identify a body part to be diagnosed by the user based on the setting data 290. After then, the electronic apparatus 100 may obtain the feature information 240, with a band pass filter (BPF), by removing a frequency domain other than the frequency domain where the auscultation sound of the body part that the user wishes to be diagnosed with is present in the auscultation sound data 210, based on the data of the remaining frequency domain.

For example, if the user wants to be diagnosed with a heart-related disease, the electronic apparatus 100 may remove a frequency domain other than 20 to 300 Hz, which is a frequency domain in which heart sounds exist, from the auscultation sound data 210 by using the BPF, and may obtain the feature information 240 based on data in the range of 20 to 300 Hz. Alternatively, if the user wishes that a disease related to the lung is diagnosed, the electronic apparatus 100 may remove a frequency domain other than 100 to 1500 Hz, which is a frequency domain in which lung sounds exist, from the auscultation sound data 210 by using the BPF, and obtain the feature information 240 based on data in the range of 100 to 1500 Hz.

According to an example embodiment, the electronic apparatus 100 may obtain the auscultation position information 250 based on the auscultation position data 220. After then, the electronic apparatus 100 may generate the combined information 270 by combining the feature information 240 and the auscultation position information 250.

According to an example embodiment, the AI model 200 may include a plurality of AI models 202, 204 and 206, and each of the plurality of AI models 202, 204 and 206 may be trained based on auscultation sound data and auscultation position data according to different body parts or different species. For example, the first AI model 202 may be trained based on heart sound data, auscultation position data of heart sound and disease data related to heart, the second AI model 204 may be trained base on lung sound data, auscultation position data of a lung sound and disease data related to lungs, and the third AI model 206 may be trained based on intestine sound data, auscultation position data for intestine sound and disease data related to intestine. Alternatively, a fourth AI model may be trained based on heart sound data of a dog, auscultation position data of heart sound of a dog and disease data related to heart of a dog, and a fifth AI model may be trained based on heart sound data of a cat, auscultation position data of heart sound of a cat and disease data related to heart of a cat. However, these are example embodiments, and data that can be used to train an AI model is not limited to the above example embodiments.

According to an example embodiment, using the AI model selected based on the setting data among the plurality of AI models 202, 204 and 206 included in the AI model 200, the electronic apparatus 100 may identify at least one of disease information 280 corresponding to the combined information 270. More specifically, the electronic apparatus 100 may identify a body part to be diagnosed by the user based on the setting data 290, input the combined information 270 into an AI model corresponding to the body part on which the user withes to receive diagnosis, and identify at least one pieces of disease information 280 output from the AI model.

For example, if the user wishes that a heart-related disease is diagnosed, the electronic apparatus 100 may input the combined information 270 to the first AI model 202 trained based on heart sound data, and identify the disease information 280 about at least one heart that is output from the first AI model 202. Alternatively, if the user wishes that a lung-related disease is diagnosed, the electronic apparatus 100 may input the combined information 270 to the second AI model 204 trained based on lung sound data, and identify at least one of disease information 280 about a lung that is output from the second AI model 204. As such, if the user wishes to receive diagnosis for a specific body part, the electronic apparatus 100 may classify diseases with higher accuracy by using an AI model trained based on data on the corresponding body part.

FIGS. 3A to 3D are diagrams for explaining a process of classifying a disease by the electronic apparatus 100 according to an example embodiment. Content overlapping descriptions with respect to FIGS. 2A to 2C will be briefly described or omitted.

Figure 3A:
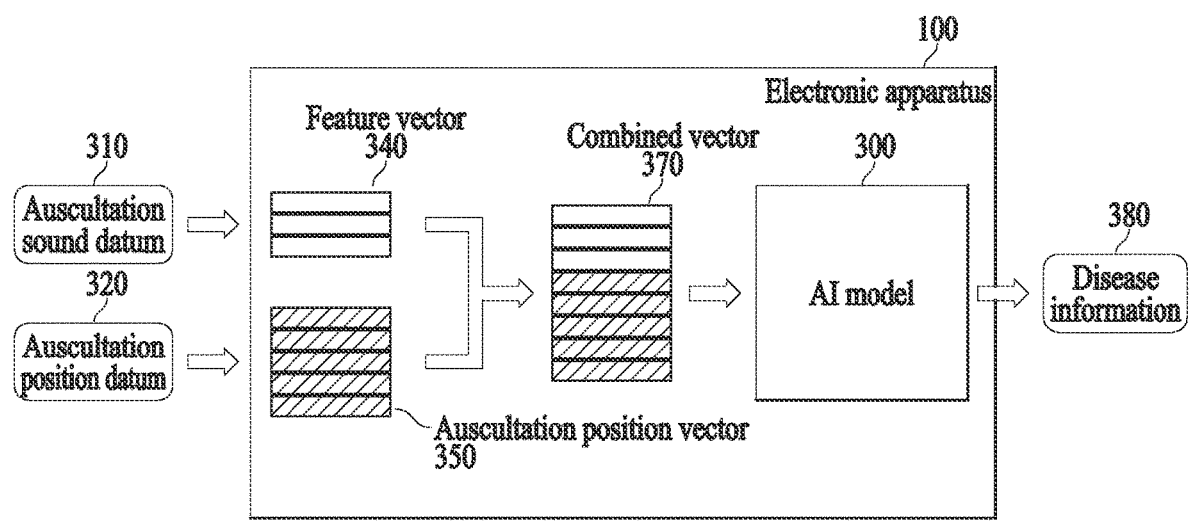
FIGS. 3A to 3D are diagrams for explaining a process of classifying a disease by an electronic apparatus according to an example embodiment.

Referring to FIG. 3A, the electronic apparatus 100 may obtain an auscultation sound datum 310 and an auscultation position datum 320 according to the example embodiment. For example, a user terminal may obtain the auscultation sound datum 310 and the auscultation position datum 320 from a smart stethoscope, or may obtain a user input that is received by a direct selection for an auscultation position from among possible auscultation positions displayed on the display of the user terminal, and may transmit the obtained auscultation sound datum 310 and the auscultation position datum 320 to the electronic apparatus 100.

According to an example embodiment, the electronic apparatus 100 may obtain a feature vector 340 based on the auscultation sound datum 310. For example, the electronic apparatus 100 may change the obtained auscultation sound datum 310 into a spectrogram image, and may obtain the feature vector 340 using an AI model.

According to an example embodiment, the electronic apparatus 100 may obtain an auscultation position vector 350 based on the auscultation position datum 320. For example, the electronic apparatus 100 may obtain the auscultation position vector 350 by embedding the auscultation position datum 320, and the size of the auscultation position vector 350 may be determined differently depending on which body part of disease the user wishes to diagnose, or whether the user intends to diagnose a disease related to an animal. With regard thereto, it will be described in detail with reference to FIGS. 5A to 5F, and FIGS. 6A and 6B.

According to an example embodiment, the electronic apparatus 100 may generate a combined vector 370 by concatenating the feature vector 340 and the auscultation position vector 350. For example, if the size of the feature vector 340 is N and the size of the auscultation position vector 350 is M, the electronic apparatus 100 may generate the combined vector 370 having a size of (N+M) by concatenating the feature vector 340 and the auscultation position vector 350.

According to an example embodiment, the electronic apparatus 100 may identify at least one of disease information 380 corresponding to the combined vector 370, using an AI model 300. For example, the electronic apparatus 100 may input the generated combined vector 370 to the AI model 300 and identify at least one of disease information 380 output from the AI model 300.

Figure 3B:
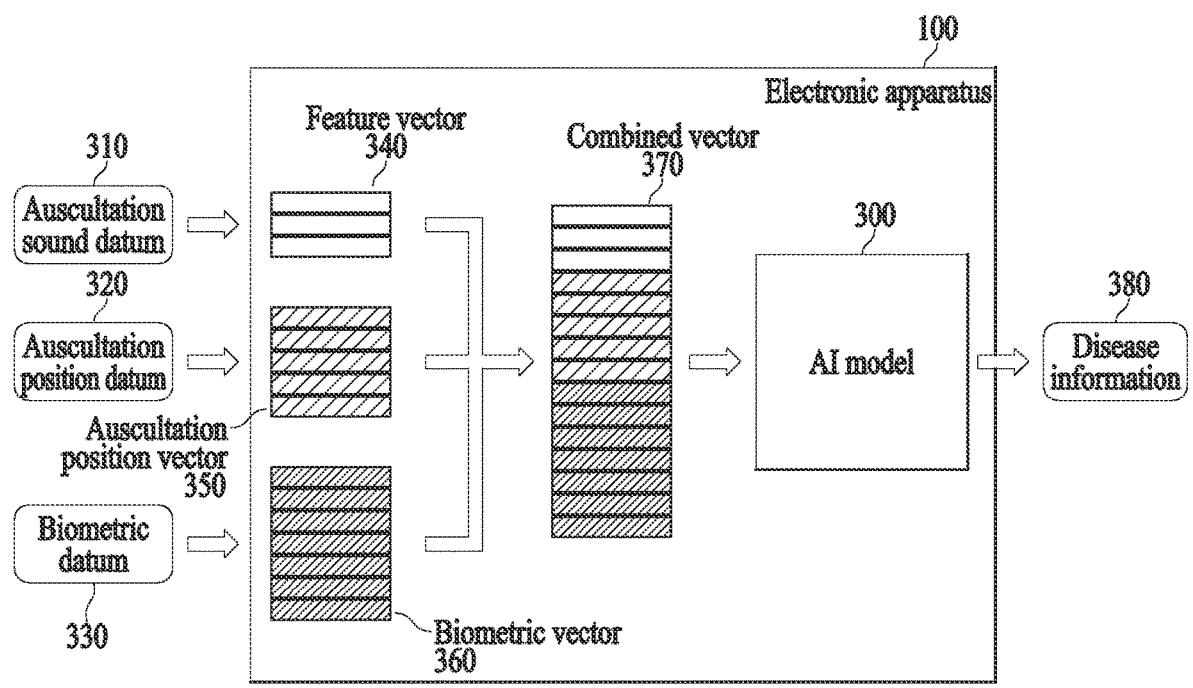

Referring to FIG. 3B, the electronic apparatus 100 may obtain the auscultation sound datum 310, the auscultation position datum 320 and a biometric datum 330 according to the example embodiment. For example, using a user terminal, a user may measure the biometric datum 330 including heart beat regularity, respiration rate, respiratory regularity, body temperature, age, blood pressure and blood sugar or the user may directly input the biometric datum 330 into the user terminal, and the user terminal may transmit the obtained biometric datum 330 to the electronic apparatus 100.

According to an example embodiment, the electronic apparatus 100 may obtain the feature vector 340 based on the auscultation sound datum 310, obtain the auscultation position vector 350 based on the auscultation position datum 320, and obtain a biometric vector 360 based on the biometric datum 330. For example, the electronic apparatus 100 may obtain the biometric vector 360 by embedding the biometric datum 330, and the size of the biometric vector 360 may be determined differently according to values that are set as the number of types of biometric data and the number of categories corresponding to each type of biometric data. With regard thereto, it will be described in detail with reference to FIG. 7.

According to an example embodiment, the electronic apparatus 100 may generate the combined vector 370 by concatenating the feature vector 340, the auscultation position vector 350 and the biometric vector 360. For example, if the size of the feature vector 340 is N, the size of the auscultation position vector 350 is M and the size of the biometric vector 360 is L, the electronic apparatus 100 may generate the combined vector 370 having a size of (N+M+L) by concatenating the feature vector 340, the auscultation position vector 350 and the biometric vector 360.

According to an example embodiment, the electronic apparatus 100 may identify at least one of disease information 380 corresponding to the combined vector 370, using the AI model 300. For example, the electronic apparatus 100 may input the generated combined vector 370 to the AI model 300, and identify at least one of disease information 380 output from the AI model 300.

Figure 3C:
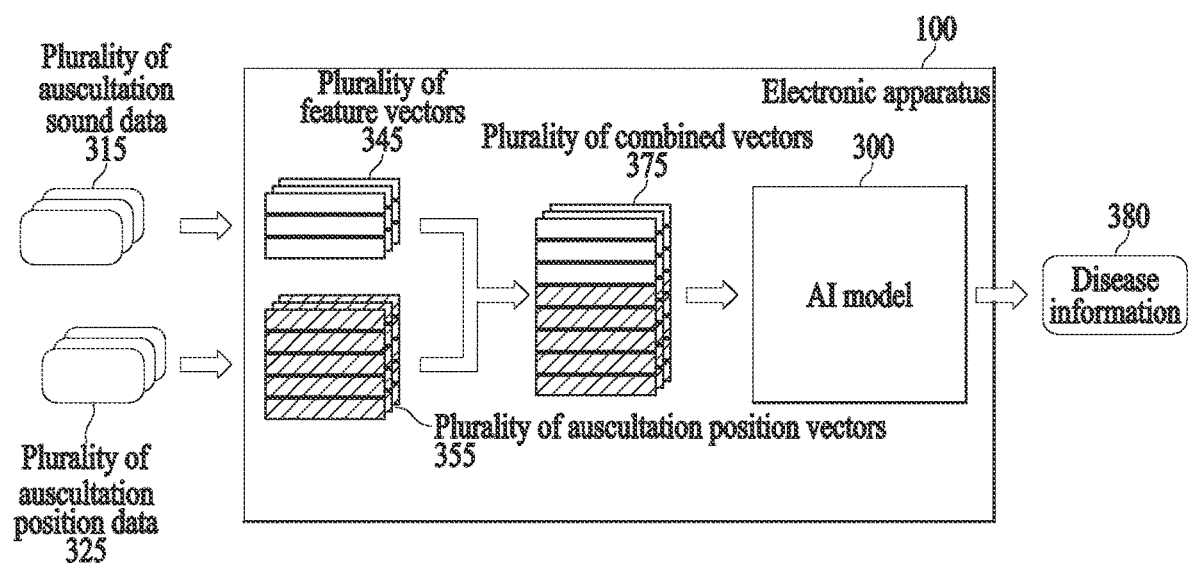

Referring to FIG. 3C, the electronic apparatus 100 may obtain a plurality of auscultation sound data 315 and a plurality of auscultation position data 325 corresponding to the example embodiment. Here, each of the plurality of auscultation sound data 315 and the plurality of auscultation position data 325 may be paired with corresponding data. For example, the plurality of auscultation sound data 315 and the plurality of auscultation position data 325 may be obtained in the form of (auscultation sound datum, auscultation position datum).

According to an example embodiment, auscultation position datum included in the plurality of auscultation position data 325 may have the same value or different values. For example, the plurality of auscultation sound data 315 and the plurality of auscultation position data 325 may include data such as (first auscultation sound datum, first auscultation position datum), (second auscultation sound datum, second auscultation position datum) or (third auscultation sound datum, third auscultation position data). Alternatively, the plurality of auscultation sound data 315 and the plurality of auscultation position data 325 may include data such as (first auscultation sound datum, first auscultation position datum), (second auscultation sound datum, first auscultation position datum) or (third auscultation sound datum, second auscultation position datum).

According to an example embodiment, the electronic apparatus 100 may obtain a plurality of feature vectors 345 based on the plurality of auscultation sound data 315. For example, the electronic apparatus 100 may convert n number of auscultation sound data 315 into a spectrogram image, and then obtain n number of feature vectors 345 by using an AI model.

According to an example embodiment, the electronic apparatus 100 may obtain a plurality of auscultation position vectors 355 based on the plurality of auscultation position data 325. For example, the electronic apparatus 100 may obtain n number of auscultation position vectors 355 by embedding n number of auscultation position data 355.

According to an example embodiment, the electronic apparatus 100 may generate a plurality of combined vectors 375 by concatenating a plurality of feature vectors 345 and a plurality of auscultation position vectors 355. For example, the electronic apparatus 100 may generate n number of combined vectors 375 by concatenating n number of feature vectors 345 and n number of auscultation position vectors 355 with corresponding vectors.

According to an example embodiment, the electronic apparatus 100 may identify at least one of disease information 380 corresponding to the plurality of combined vectors 375, using the AI model 300. For example, the electronic apparatus 100 may input the generated plurality of combined vectors 375 to the AI model 300, and may identify at least one of disease information 380 output from the AI model 300.

Figure 3D:
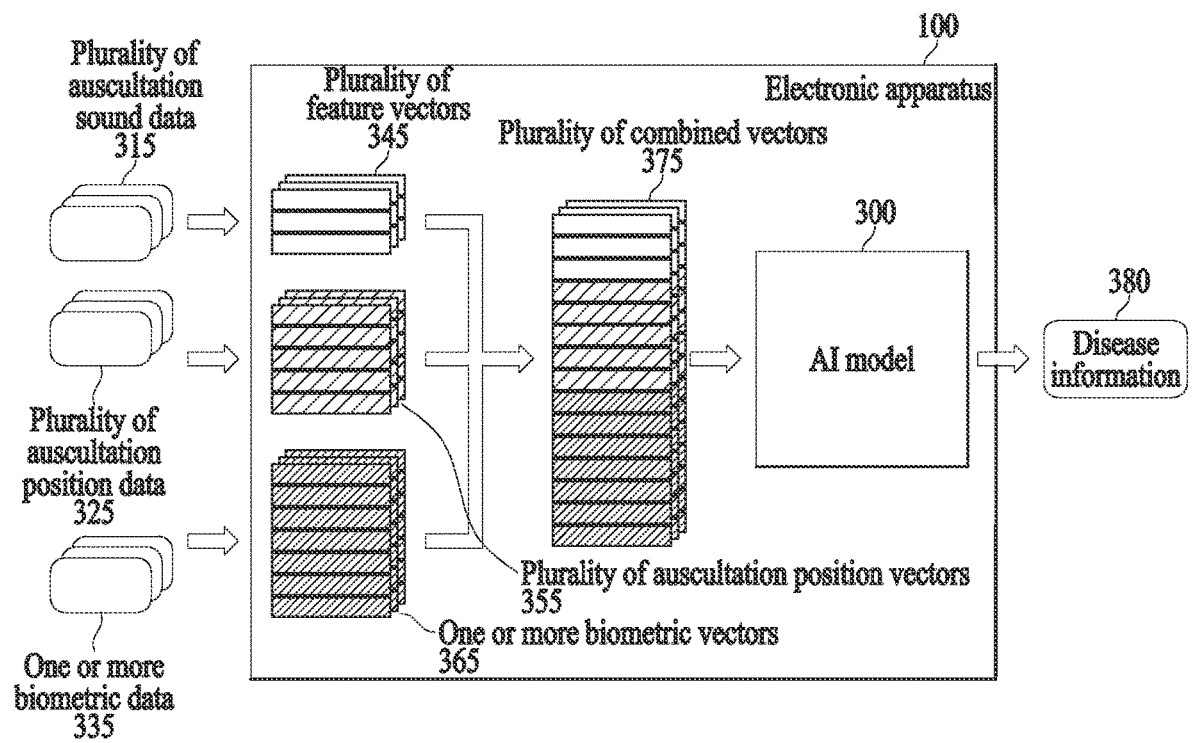

Referring to FIG. 3D, the electronic apparatus 100 may obtain the plurality of auscultation sound data 315, the plurality of auscultation position data 325 and one or more biometric data 335 according to the example embodiment. Here, one or more biometric data 335 may be one or plural. For example, if the biometric data 335 includes data measured every time auscultation sound data is obtained, the electronic apparatus 100 may obtain the plurality of biometric data 335 corresponding to each of a plurality of auscultation sound data. On the other hand, if the biometric data 335 does not include data measured every time auscultation sound data is obtained but the same data value is used (for example, age), the electronic apparatus 100 may obtain one of the biometric data 335.

According to an example embodiment, the electronic apparatus 100 may obtain a plurality of feature vectors 345 based on the plurality of auscultation sound data 315, obtain a plurality of auscultation position vectors 355 based on the plurality of auscultation position data 325, and obtain one or more biometric vectors 365 based on one or more biometric data 335. For example, the electronic apparatus 100 may obtain n number of feature vectors 345 based on n number of auscultation sound data 315, and may obtain n number of auscultation position vectors 355 by embedding n number of auscultation position data 325. Alternatively, the electronic apparatus 100 may obtain one or more biometric vectors 365 by embedding one or more biometric data 335.

According to an example embodiment, the electronic apparatus 100 may generate the plurality of combined vectors 375 by concatenating the plurality of feature vectors 345, the plurality of auscultation position vectors 355 and one or more biometric vectors 365. For example, if one or more biometric data 335 includes data measured every time auscultation sound data is obtained, the electronic apparatus 100 may generate n number of combined vectors 375, by concatenating n number of feature vectors 345, n number of auscultation position vectors 355 and n number of biometric vectors 365 with corresponding vectors. Alternatively, if one or more biometric data 335 does not include data measured every time auscultation sound data is obtained but the same data value is used, the electronic apparatus 100 may concatenate each of n number of feature vectors 345 to corresponding n number of auscultation position vectors 355, and concatenate one of the biometric vectors 365 to each of n number of vectors to which the feature vectors and the auscultation position vectors are concatenated, to generate n number of combined vectors 375.

According to an example embodiment, the electronic apparatus 100 may identify at least one of disease information 380 corresponding to the plurality of combined vectors 375, using the AI model 300. For example, the electronic apparatus 100 may input the generated plurality of combined vectors 375 to the AI model 300, and may identify at least one of disease information 380 output from the AI model 300.

FIGS. 4A to 4D are diagrams for explaining a process of classifying a disease by the electronic apparatus 100 according to an example embodiment. Content overlapping descriptions with respect to FIGS. 3A to 3D will be briefly described or omitted.

Figure 4A:
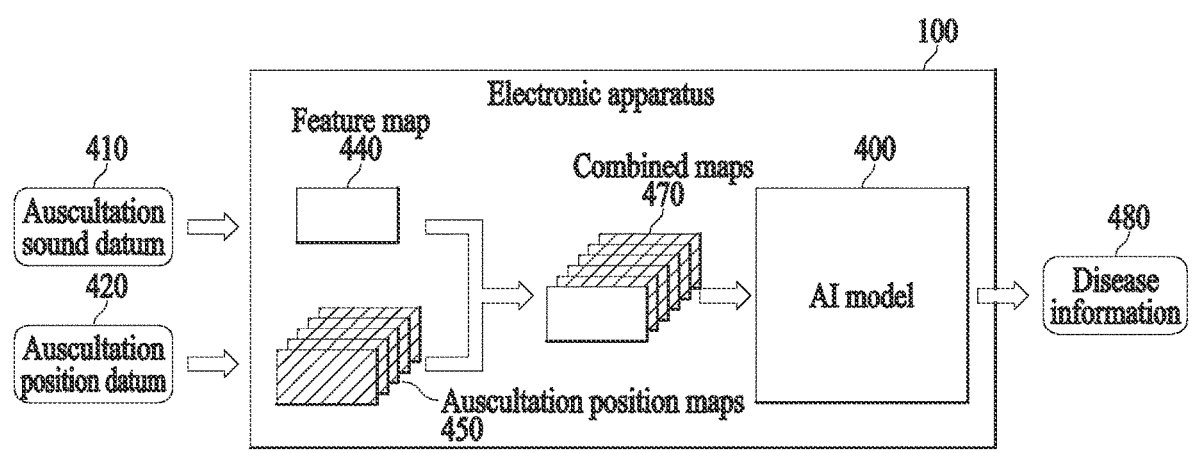
FIGS. 4A to 4D are diagrams for explaining a process of classifying a disease by an electronic apparatus according to an example embodiment.

Referring to FIG. 4A, the electronic apparatus 100 may obtain an auscultation sound datum 410 and an auscultation position datum 420 according to the example embodiment. For example, a user terminal may obtain the auscultation sound datum 410 and the auscultation position datum 420 from a smart stethoscope, or may obtain a user input that is received by a direct selection for an auscultation position from among possible auscultation positions displayed on the display of the user terminal, and may transmit the obtained auscultation sound datum 410 and the auscultation position datum 420 to the electronic apparatus 100.

According to an example embodiment, the electronic apparatus 100 may obtain a feature map 440 based on the auscultation sound datum 410. For example, the electronic apparatus 100 may obtain the feature map 440 by using an AI model after changing the obtained auscultation sound datum 410 into a spectrogram image.

According to an example embodiment, the electronic apparatus 100 may obtain auscultation position maps 450 based on the auscultation position datum 420. For example, the electronic apparatus 100 may obtain the auscultation position maps 450 based on the auscultation position datum 420, and the number of maps included in the auscultation position maps 450 may be determined differently depending on depending on which body part of disease the user wishes to diagnose, or whether the user intends to diagnose a disease related to an animal. With regard thereto, it will be described in detail with reference to FIGS. 8A to 8F and FIGS. 9A to 9C.

According to an example embodiment, the electronic apparatus 100 may generate combined maps 470 by adding the auscultation position maps 450 to the feature map 440 as a channel. For example, if the number of maps included in the auscultation position maps 450 is M, the electronic apparatus 100 may generate the combined maps 470 including (M+1) maps by adding the auscultation position maps 450 to the feature map 440 as a channel.

According to an example embodiment, the electronic apparatus 100 may identify at least one of disease information 480 corresponding to the combined maps 470, using an AI model 400. For example, the electronic apparatus 100 may input the generated combined maps 470 to the AI model 400, and may identify at least one of disease information 480 output from the AI model 400.

Figure 4B:
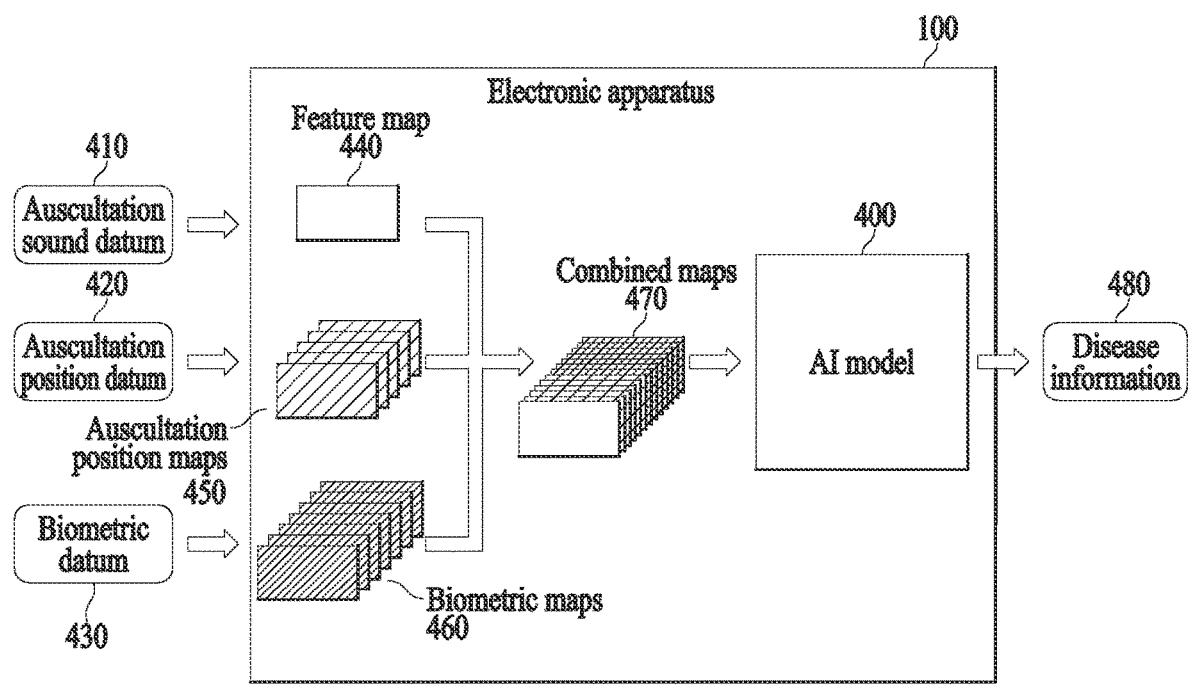

Referring to FIG. 4B, the electronic apparatus 100 may obtain the auscultation sound datum 410, the auscultation position datum 420 and a biometric datum 430 according to the example embodiment. For example, a user may measure the biometric datum 430 including heart beat regularity, respiration rate, respiratory regularity, body temperature, age, blood pressure and blood sugar using a user terminal, or may directly input the biometric datum 430 into the user terminal, and the user terminal may transmit the obtained biometric datum 430 to the electronic apparatus 100.

According to an example embodiment, the electronic apparatus 100 may obtain the feature map 440 based on the auscultation sound datum 410, obtain the auscultation position maps 450 based on the auscultation position datum 420, and obtain biometric maps 460 based on the biometric datum 430. For example, the electronic apparatus 100 may obtain the biometric maps 460 based on the biometric datum 430, and the number of maps included in the biometric maps 460 may be determined differently according to values that are set as the number of types of biometric data and the number of categories corresponding to each type of biometric data. With regard thereto, it will be described in detail with reference to FIG. 10.

According to an example embodiment, the electronic apparatus 100 may generate the combined maps 470 by adding the auscultation position maps 450 and the biometric maps 460 to the feature map 440 as channels. For example, if the number of maps contained in the auscultation position maps 450 is M and the number of maps contained in the biometric maps 460 is L, the electronic apparatus 100 may generate the combined maps 470 including (M+L+1) maps by adding the auscultation position maps 450 and the biometric maps 460 to the feature map 440 as channels.

According to an example embodiment, the electronic apparatus 100 may identify at least one of disease information 480 corresponding to the combined maps 470, using the AI model 400. For example, the electronic apparatus 100 may input the generated combined maps 470 to the AI model 440, and may identify at least one of disease information 480 output from the AI model 400.

Figure 4C:
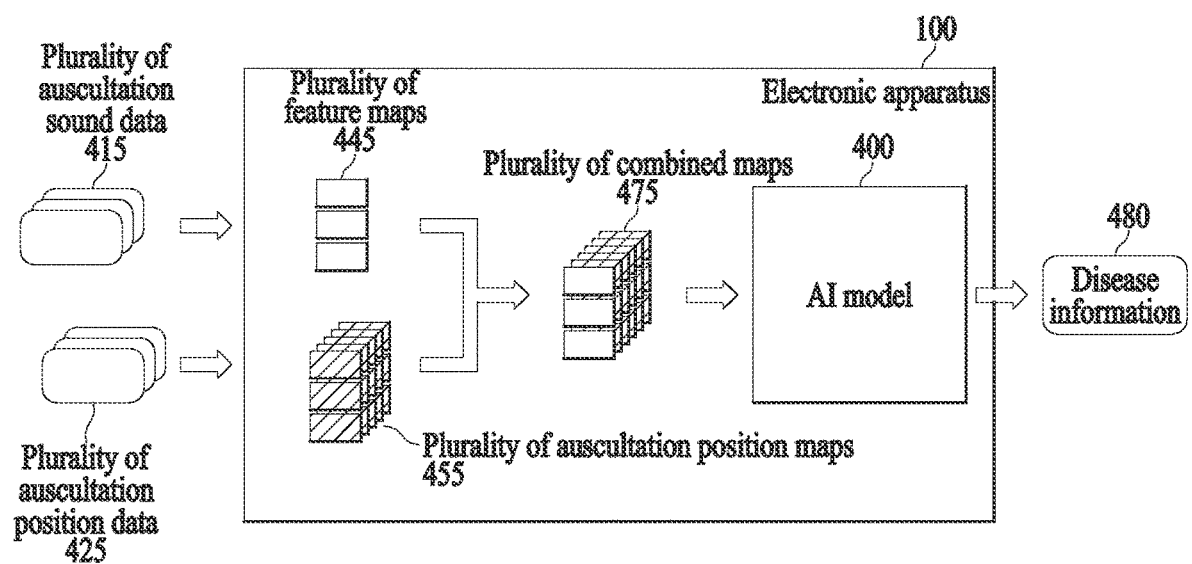

Referring to FIG. 4C, the electronic apparatus 100 may obtain a plurality of auscultation sound data 415 and a plurality of auscultation position data 425 according to the example embodiment. Here, each of the plurality of auscultation sound data 415 and the plurality of auscultation position data 425 may be paired with corresponding data. For example, the plurality of auscultation sound data 415 and the plurality of auscultation position data 425 may be obtained in the form of (auscultation sound datum, auscultation position datum).

According to an example embodiment, the electronic apparatus 100 may obtain a plurality of feature maps 445 based on the plurality of auscultation sound data 415. For example, the electronic apparatus 100 may convert n number of auscultation sound data 415 into a spectrogram image and then obtain n number of feature maps 445 by using an AI model.

According to an example embodiment, the electronic apparatus 100 may obtain a plurality of auscultation position maps 455 based on the plurality of auscultation position data 425. For example, the electronic apparatus 100 may obtain n number of auscultation positions maps 455 based on n number of auscultation position data 425.

According to an example embodiment, the electronic apparatus 100 may generate a plurality of combined maps 475 by adding the plurality of auscultation position maps 455 to the plurality of feature maps 445 as a channel. For example, the electronic apparatus 100 may generate n number of combined maps 475 by adding n number of auscultation position maps 455 corresponding to each of the n number of feature maps 445 as channels.

According to an example embodiment, the electronic apparatus 100 may identify at least one of disease information 480 corresponding to the plurality of combined maps 475, using the AI model 400. For example, the electronic apparatus 100 may input the generated plurality of combined maps 475 to the AI model 400, and may identify at least one of disease information 480 output from the AI model 400.

Figure 4D:
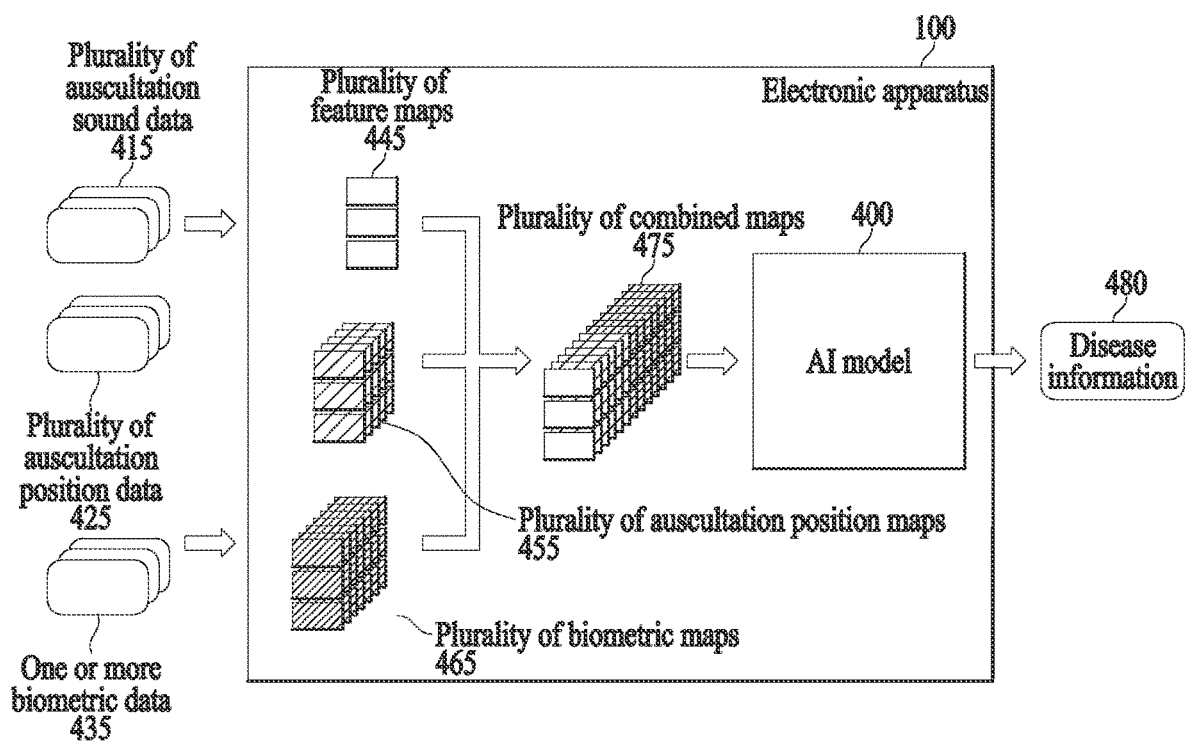

Referring to FIG. 4D, the electronic apparatus 100 may obtain the plurality of auscultation sound data 415, the plurality of auscultation position data 425 and one or more biometric data 435 according to the example embodiment. Here, one or more biometric data 435 may be one or plural. For example, if the biometric data 435 includes data measured every time auscultation sound data is obtained, the electronic apparatus 100 may obtain the plurality of biometric data 435 corresponding to each of a plurality of auscultation sound data. On the other hand, if the biometric data 435 does not include data measured every time auscultation sound data is obtained but the same data value is used, the electronic apparatus 100 may obtain one of the biometric data 435.

According to an example embodiment, the electronic apparatus 100 may obtain the plurality of feature maps 445 based on the plurality of auscultation sound data 415, may obtain the plurality of auscultation position maps 455 based on the plurality of auscultation position data 425, and may obtain a plurality of biometric maps 465 based on one or more biometric data 435. For example, the electronic apparatus 100 may obtain n number of feature maps 445 based on n number of auscultation sound data 415, and may obtain n number of auscultation position maps 455 based on n number of auscultation position data 425. Alternatively, the electronic apparatus 100 may obtain the plurality of biometric maps 465 by embedding one or more biometric data 435.

According to an example embodiment, the electronic apparatus 100 may generate the plurality of combined maps 475 by adding the plurality of auscultation position maps 455 and one or more feature maps 465 to the plurality of feature maps 445 as channels. For example, if one or more biometric data 435 includes data measured every time auscultation sound data is obtained, the electronic apparatus 100 may generate n number of combined maps 475 by adding n number of auscultation position maps 455 and n number of biometric maps 465 corresponding to each of then number of feature maps 445 as channels. Alternatively, if one or more biometric data 435 does not include data measured every time auscultation sound data is obtained but the same data value is used, the electronic apparatus 100 may add n number of auscultation position maps 455 corresponding to each of the n number of feature maps 445 as channels, and may generate n number of combined maps 475 by adding one of the biometric maps 465 as a channel.

According to an example embodiment, the electronic apparatus 100 may identify at least one of disease information 480 corresponding to the plurality of combined maps 475 using the AI model 400. For example, the electronic apparatus 100 may input the generated plurality of combined maps 475 to the AI model 400, and may identify at least one of disease information 480 output from the AI model 400.

FIGS. 5A to 5F are diagrams for explaining a process in which the electronic apparatus 100 obtains auscultation position vectors based on auscultation position data according to an example embodiment.

Figure 5A:
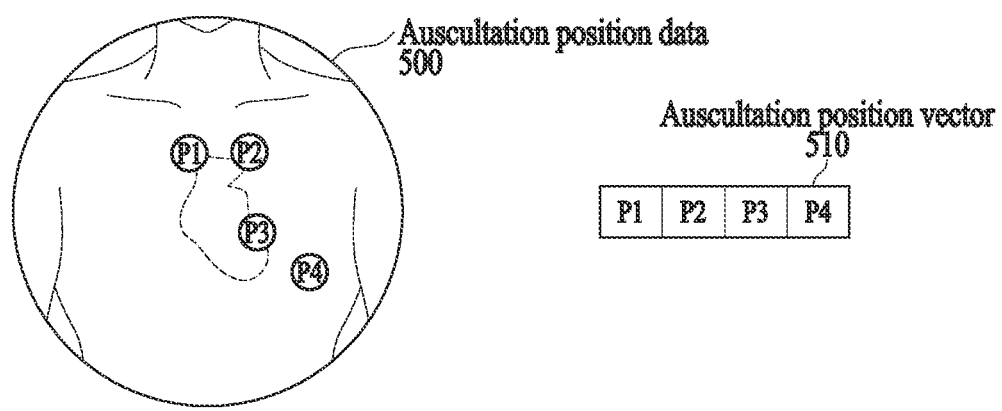
FIGS. 5A to 5F are diagrams for explaining a process in which an electronic apparatus obtains auscultation position vectors based on auscultation position data according to an example embodiment.

Referring to FIG. 5A, the electronic apparatus 100 may obtain auscultation position data 500 according to the example embodiment. For example, the electronic apparatus 100 may obtain the auscultation position data 500 including data about a position where heart sound is measured among positions where heart sound can be auscultated. Here, positions where heart sound can be auscultated may include positions P1, P2, P3 and P4, and the auscultation position data 500 may include data about positions where heart sound are measured among P1, P2, P3 and P4.

According to an example embodiment, the position where heart sound can be auscultated may include a body part where the stethoscope is placed in order to diagnose a heart disease. For example, P1 may represent the location of the aortic valve where the second intercostal space (ICS) and the upper right parasternal border are, and P2 may represent the location of the pulmonic valve where the second ICS and the upper left parasternal border are. Further, P3 may indicate the location of the tricuspid valve where the fourth or fifth ICS and the lower left parasternal border are, and P4 may indicate the location of the mitral valve or bicuspid valve where the fifth ICS and the medial left mid-clavicular line are. However, the positions are example embodiments, and body parts where the stethoscope is placed to diagnose heart disease is not limited to the example embodiments.

According to an example embodiment, the electronic apparatus 100 may identify a position where an auscultation can be performed based on the auscultation position data 500 or setting data. For example, if the auscultation position data 500 includes auscultation position data of heart sound, the electronic apparatus 100 may identify a position where heart sound can be auscultated as a position where auscultation can be performed. Alternatively, if the setting data includes a user input for diagnosis related to a heart-related disease, the electronic apparatus 100 may obtain setting data, and may identify a position where heart sound can be auscultated as a position where an auscultation can by performed based on the setting data.

According to an example embodiment, the electronic apparatus 100 may obtain auscultation position vector 510 by embedding the auscultation position data 500. Here, if the number of identified positions where the auscultation can be performed is n, the electronic apparatus 100 may obtain the auscultation position vector 510 having a size of n. For example, if positions where heart sound can be auscultated are 4, the electronic apparatus 100 may obtain the auscultation position vector 510 having the size of 4, and components of the auscultation position vector 510 may each correspond to positions where heart sound can be auscultated.

According to an example embodiment, among the components included in the auscultation position vector 510, a component corresponding to the auscultation position has a first value, the remaining components may have a second value. For example, if the auscultation position data 500 includes auscultation position data corresponding to P2, among the components included in the auscultation position vector 510, a component corresponding to P2 may have a first value, and the remaining components may have a second value. In other words, the auscultation position vector 510 may be expressed as [a second value, a first value, a second value, a second value]. Here, the first value may include 1 and the second value may include 0.

According to an example embodiment, the electronic apparatus 100 may identify an AI model to be used based on the auscultation position data 500 or setting data. For example, if the auscultation position data 500 includes auscultation position data of heart sound, the electronic apparatus 100 may use an AI model trained based on heart sound data, auscultation position data of heart sound and heart disease data. Alternatively, if the setting data includes a user input for diagnosis related to a heart-related disease, the electronic apparatus 100 may use an AI model trained based on heart sound data, auscultation position data of heart sound and heart disease data.

Figure 5B:
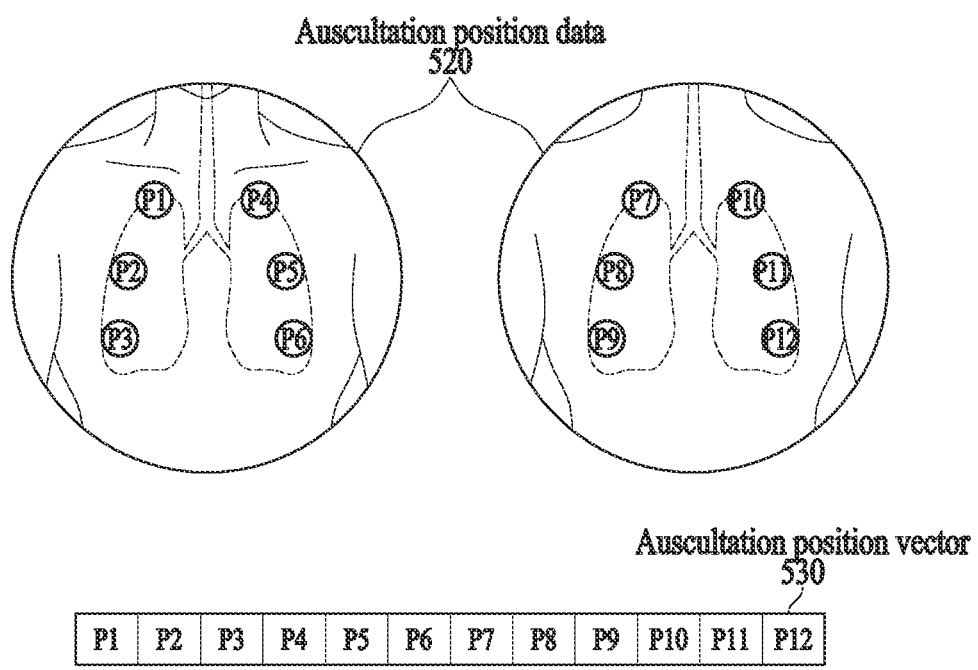

Referring to FIG. 5B, the electronic apparatus 100 may obtain auscultation position data 520 according to the example embodiment. For example, the electronic apparatus 100 may obtain the auscultation position data 520 including data about a position where lung sounds are measured among positions where a lung sound can be auscultated. Here, the positions where a lung sound can be auscultated may include positions P1 to P12, and the auscultation position data 520 may include data on positions where lung sounds are measured among P1 to P12.

According to an example embodiment, a position where a lung sound can be auscultated may indicate a body part where a stethoscope is placed to diagnose a disease related to the lungs. For example, P1 may represent the front right upper position, and P5 may represent the front left middle position. Further, P9 may indicate a lower left position of the rear surface or the back, and P10 may indicate an upper right position of the rear surface or the back. However, the positions are mere example embodiments, and the body part where the stethoscope is placed to diagnose diseases related to the lungs is not limited to the example embodiments.

According to an example embodiment, the electronic apparatus 100 may identify positions where an auscultation can be performed based on the auscultation position data 520 or setting data. For example, if the auscultation position data 520 includes auscultation position data of lung sound, the electronic apparatus 100 may identify a position where a lung sound can be auscultated as a position where auscultation can be performed. Alternatively, if the setting data includes a user input for diagnosis related to a lung-related disease, the electronic apparatus 100 may obtain setting data, and may identify a position where a lung sound can be auscultated as a position where an auscultation can be performed based on the setting data.

According to an example embodiment, the electronic apparatus 100 may obtain auscultation position vector 530 by embedding the auscultation position data 520. Here, if the number of identified positions where an auscultation can be performed is n, the electronic apparatus 100 may obtain the auscultation position vector 530 of size n. For example, if positions where a lung sound can be auscultated are 12, the electronic apparatus 100 may obtain the auscultation position vector 530 having a size of 12, and each component of the auscultation position vector 530 may correspond to a position where a lung sound can be auscultated.

According to an example embodiment, among the components included in the auscultation position vector 530, a component corresponding to the auscultation position may have a first value, and the remaining components may have a second value. For example, if the auscultation position data 520 includes auscultation position data corresponding to P7, among the components included in the auscultation position vector 530, a component corresponding to P7 may have a first value, and the remaining components may have a second value. In other words, the auscultation position vector 530 may be expressed as [a second value, a second value, a second value, a second value, a second value, a second value, a first value, a second value, a second value, a second value, a second value, a second value]. Here, the first value may include 1, and the second value may include 0.

According to an example embodiment, the electronic apparatus 100 may identify an AI model to be used based on the auscultation position data 520 or setting data. For example, if the auscultation position data 520 includes auscultation position data of lung sound, the electronic apparatus 100 may use an AI model trained based on lung sound data, auscultation position data of lung sound and lung disease data. Alternatively, if the setting data includes a user input for diagnosis related to a lung-related disease, the electronic apparatus 100 may use an AI model trained based on lung sound data, auscultation position data of lung sound and lung disease data.

Figure 5C:
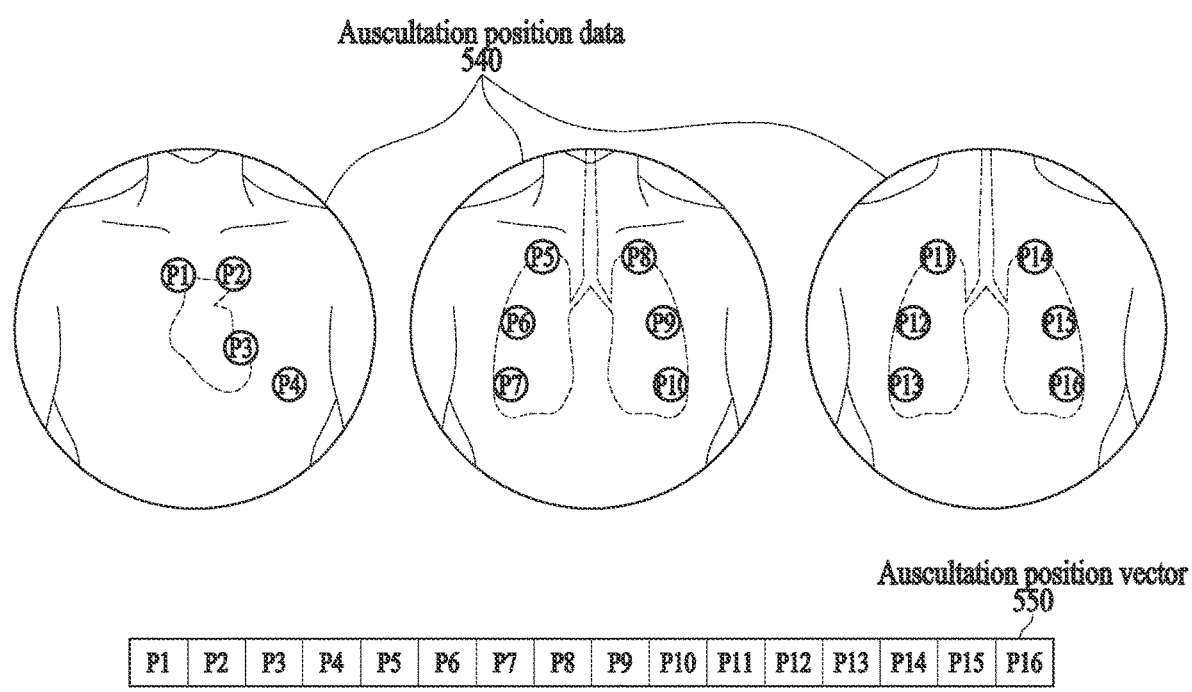

Referring to FIG. 5C, the electronic apparatus 100 may obtain auscultation position data 540 according to the example embodiment. For example, the electronic apparatus 100 may obtain the auscultation position data 540 including data about a position where the auscultation sound was measured, among positions where heart sound and lung sound can be auscultated. Here, the positions where a heart sound can be auscultated may include positions P1 to P4. The positions where a lung sound can be auscultated may include positions P5 to P16. The auscultation position data 540 may include data about positions where auscultation sound is measured among positions P1 to P16.

According to an example embodiment, the electronic apparatus 100 may identify the positions where an auscultation can be performed based on the auscultation position data 540 or setting data. For example, if the auscultation position data 540 includes auscultation position data of heart sound or lung sound, the electronic apparatus 100 may identify a position where a heart sound or a lung sound can be auscultated as a position where an auscultation can be performed. Alternatively, if the setting data does not include a user input on the body part to be diagnosed or includes user inputs by which diseases of all body parts are to be diagnosed, the electronic apparatus 100 may obtain the setting data, and may identify positions where heart sound, lung sound, and intestine sound can be auscultated as positions where an auscultation can be performed based on the setting data. However, the positions are mere example embodiments, and a body part where an auscultation can be performed is not limited thereto.

According to an example embodiment, the electronic apparatus 100 may obtain auscultation position vector 550 by embedding the auscultation position data 540. Here, if the number of identified positions where an auscultation can be performed is n, the electronic apparatus 100 may obtain the auscultation position vector 550 of size n. For example, if positions where heart sound can be auscultated are 4, and positions where a lung sound can be auscultated are 12, the electronic apparatus 100 may obtain the auscultation position vector 550 with a size of 16, and each component of the auscultation position vector 550 may correspond to a position where a heart sound or a lung sound can be auscultated.

According to an example embodiment, among the components included in the auscultation position vector 550, a component corresponding to the auscultation position may have a first value and the remaining components may have a second value. For example, if the auscultation position data 540 includes the auscultation position data corresponding to P11, among the components included in the auscultation position vector 550, a component corresponding to P11 may have the first value, and the remaining components may have the second value. In other words, the auscultation position vector 550 may be expressed as [a second value, a second value, a second value, a second value, a second value, a second value, a second value, a second value, a second value, a second value, a first value, a second value, a second value, a second value, a second value, a second value]. Here, the first value may include 1, and the second value may include 0.

According to an example embodiment, the electronic apparatus 100 may identify an AI model to be used based on the auscultation position data 540 or setting data. For example, if the auscultation position data 540 includes auscultation position data of lung sound, the electronic apparatus 100 may use an AI trained based on one or more auscultation sound data, one or more auscultation position data and one or more disease data. Alternatively, if the setting data does not include a user input on the body part to be diagnosed, or includes user inputs by which diseases of all body parts are to be diagnosed, the electronic apparatus 100 may use an AI model trained based on one or more auscultation sound data, one or more auscultation position data and one or more disease data.

Figure 5D:
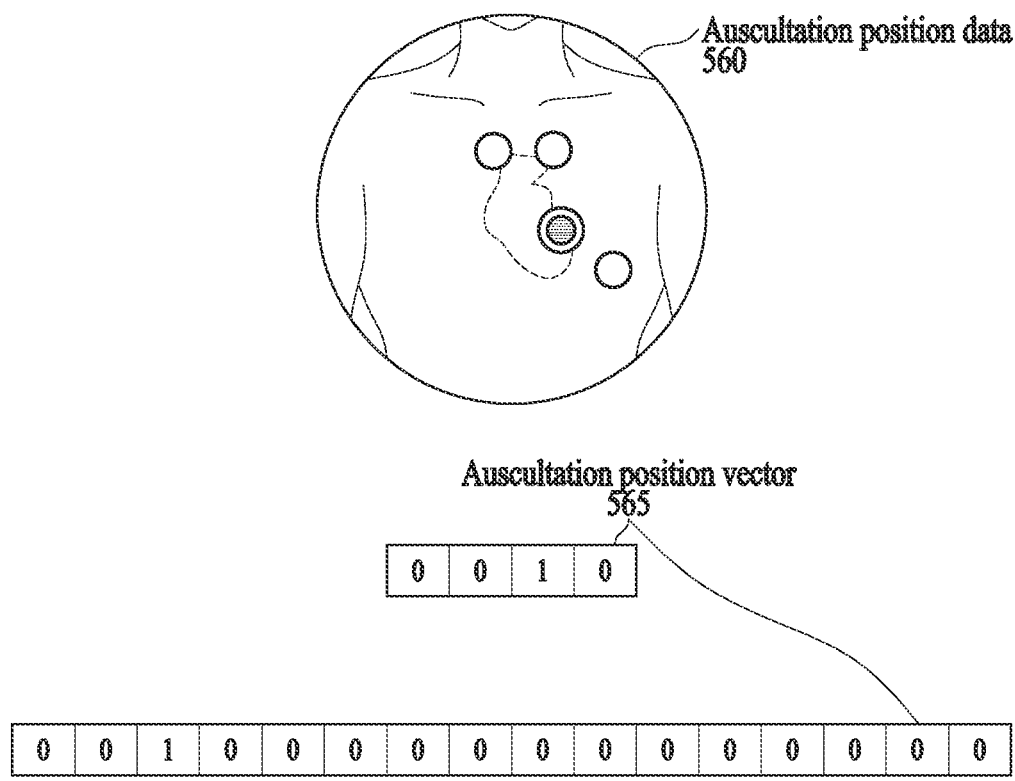

Referring to FIG. 5D, the electronic apparatus 100 may obtain auscultation position data 560 according to the example embodiment. For example, the electronic apparatus 100 may obtain the auscultation position data 560 including data that among positions where heart sound can be auscultated, the heart sound was measured at the third position.

According to an example embodiment, the electronic apparatus 100 may identify a position where an auscultation can be performed based on the auscultation position data 560. For example, as the auscultation position data 560 includes auscultation position data of heart sound, the electronic apparatus 100 may identify a position where heart sound can be auscultated as a position where an auscultation can be performed. Alternatively, as the auscultation position data 560 includes auscultation position data of heart sound, the electronic apparatus 100 may identify a position where a heart sound or a lung sound can be auscultated as a position where an auscultation can be performed.

According to an example embodiment, the electronic apparatus 100 may identify a position where an auscultation can be performed based on setting data. For example, as the setting data includes user inputs by which diseases of heart is to be diagnosed, the electronic apparatus 100 may identify a position where heart sound can be auscultated as a position where an auscultation can be performed based on the setting data. Alternatively, as the setting data does not include a user input regarding a body part for which diagnosis is to be received, or as the setting data includes user inputs by which diseases of all body parts are to be diagnosed, the electronic apparatus 100 may identify a position where a heart sound or a lung sound can be auscultated as a position where an auscultation can be performed based on the setting data.

According to an example embodiment, the electronic apparatus 100 may obtain auscultation position vector 565 by embedding the auscultation position data 560. For example, if it is identified that positions where an auscultation can be performed are 4, the electronic apparatus 100 may obtain the auscultation position vector 565 having values of [0, 0, 1, 0]. Alternatively, if it is identified that positions where an auscultation can be performed are 16, the electronic apparatus 100 may obtain the auscultation position vector 565 having values of [0, 0, 1, 0, 0, 0, 0, 0, 0, 0, 0, 0, 0, 0, 0, 0].

Figure 5E:
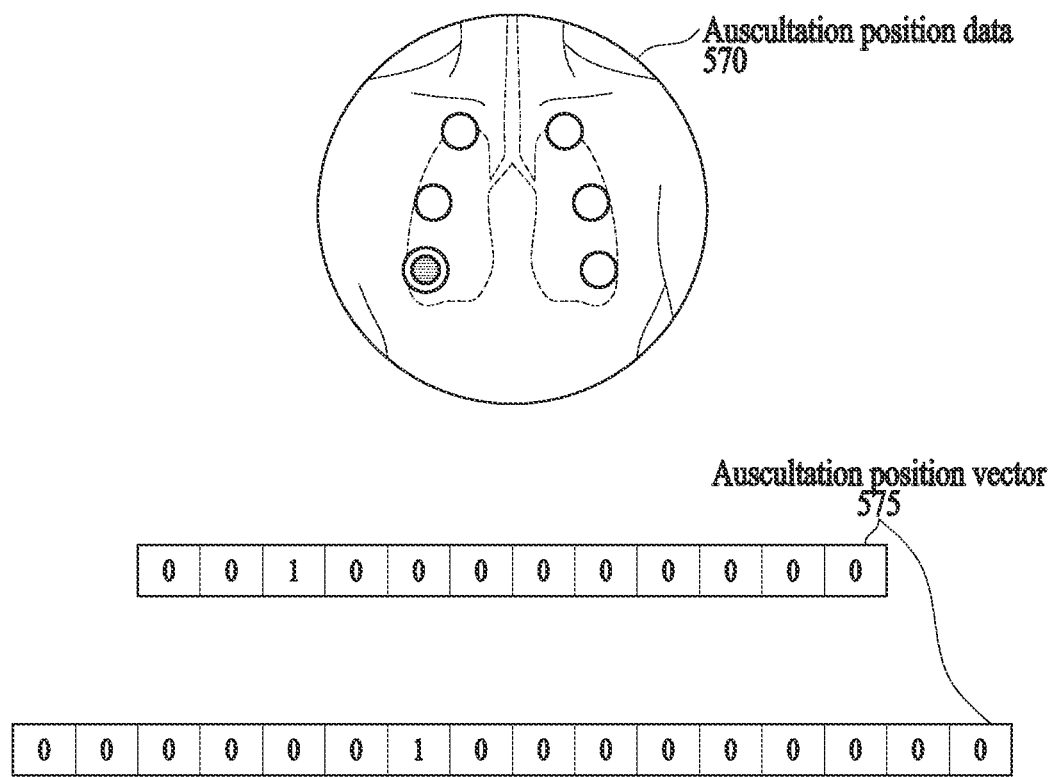

Referring to FIG. 5E, the electronic apparatus 100 may obtain auscultation position data 570 according to the example embodiment. For example, the electronic apparatus 100 may obtain the auscultation position data 570 including data that lung sounds were measured at the third position among positions where a lung sound can be auscultated.

According to an example embodiment, the electronic apparatus 100 may identify a position where an auscultation can be performed based on the auscultation position data 570. For example, as the auscultation position data 570 includes auscultation position data of lung sound, the electronic apparatus 100 may identify a position where a lung sound can be auscultated as a position where an auscultation can be performed. Alternatively, as the auscultation position data 570 includes auscultation position data of lung sound, the electronic apparatus 100 may identify a position where a heart sound or a lung sound can be auscultated as a position where an auscultation can be performed.

According to an example embodiment, the electronic apparatus 100 may identify a position where an auscultation can be performed based on the setting data. For example, as the setting data includes a user input by which diseases of lungs are to be diagnosed, the electronic apparatus 100 may identify a position where a lung sound can be auscultated as a position where an auscultation can be performed based on the setting data. Alternatively, as the setting data does not include a user input regarding a body part for which diagnosis is to be received, or as the setting data includes user inputs by which diseases of all body parts are to be diagnosed, the electronic apparatus 100 may identify a position where a heart sound or a lung sound can be auscultated as a position where an auscultation can be performed based on the setting data.

According to an example embodiment, the electronic apparatus 100 may obtain auscultation position vector 575 by embedding the auscultation position data 570. For example, if it is identified that positions where a auscultation can be performed are 12, the electronic apparatus 100 may obtain the auscultation position vector 575 having values of [0, 0, 1, 0, 0, 0, 0, 0, 0, 0, 0, 0]. Alternatively, if it is identified that positions where a auscultation can be performed are 16, the electronic apparatus 100 may obtain the auscultation position vector 575 having values of [0, 0, 0, 0, 0, 0, 0, 1, 0, 0, 0, 0, 0, 0, 0, 0].

Figure 5F:
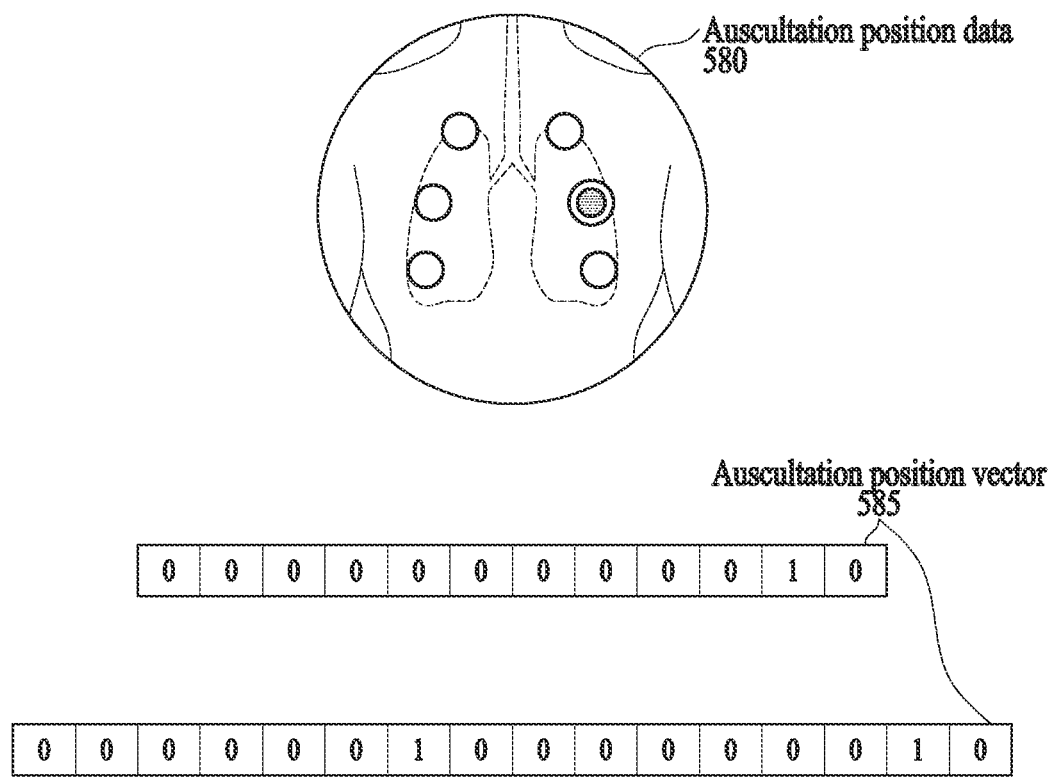

Referring to FIG. 5F, the electronic apparatus 100 may obtain auscultation position data 580 according to the example embodiment. For example, the electronic apparatus 100 may obtain the auscultation position data 580 including data that among positions where a lung sound can be auscultated, lung sound was measured at the $11^{th}$ position.

According to an example embodiment, the electronic apparatus 100 may obtain a position where an auscultation can be performed based on the auscultation position data 580. For example, as the auscultation position data 580 includes auscultation position data of lung sound, the electronic apparatus 100 may obtain a position where a lung sound can be auscultated as a position where an auscultation can be performed. Alternatively, as the auscultation position data 580 includes auscultation position data of lung sound, the electronic apparatus 100 may identify positions where a heart sound or a lung sound can be auscultated as a position where an auscultation can be performed.

According to an example embodiment, the electronic apparatus 100 may identify a position where an auscultation can be performed based on the setting data. For example, as the setting data includes a user input by which diseases of lungs are to be diagnosed, the electronic apparatus 100 may identify a position where a lung sound can be auscultated as a position where an auscultation can be performed based on the setting data. Alternatively, as the setting data does not include a user input regarding a body part for which diagnosis is to be received, or as the setting data includes user inputs by which diseases of all body parts are to be diagnosed, the electronic apparatus 100 may identify a position where a heart sound or a lung sound can be auscultated as a position where an auscultation can be performed based on the setting data.

According to an example embodiment, the electronic apparatus 100 may obtain auscultation position vector 585 by embedding the auscultation position data 580. For example, if it is identified that positions where an auscultation can be performed are 12, the electronic apparatus 100 may obtain the auscultation position vector 585 having values of [0, 0, 0, 0, 0, 0, 0, 0, 0, 0, 1, 0]. Alternatively, if it is identified that positions where an auscultation can be performed are 16, the electronic apparatus 100 may obtain the auscultation position vector 585 having values of [0, 0, 0, 0, 0, 0, 0, 0, 0, 0, 0, 0, 0, 0, 1, 0].

Figure 6A:
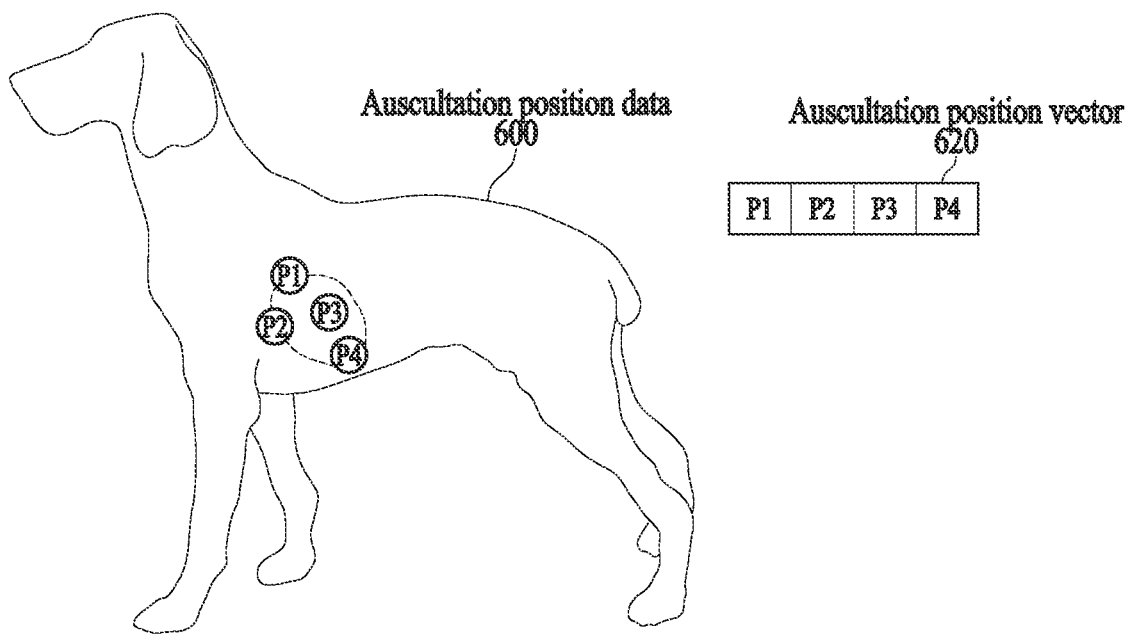
FIGS. 6A and 6B are diagrams for explaining a process of obtaining auscultation position vectors by an electronic apparatus based on auscultation position data according to an example embodiment.
Figure 6B:
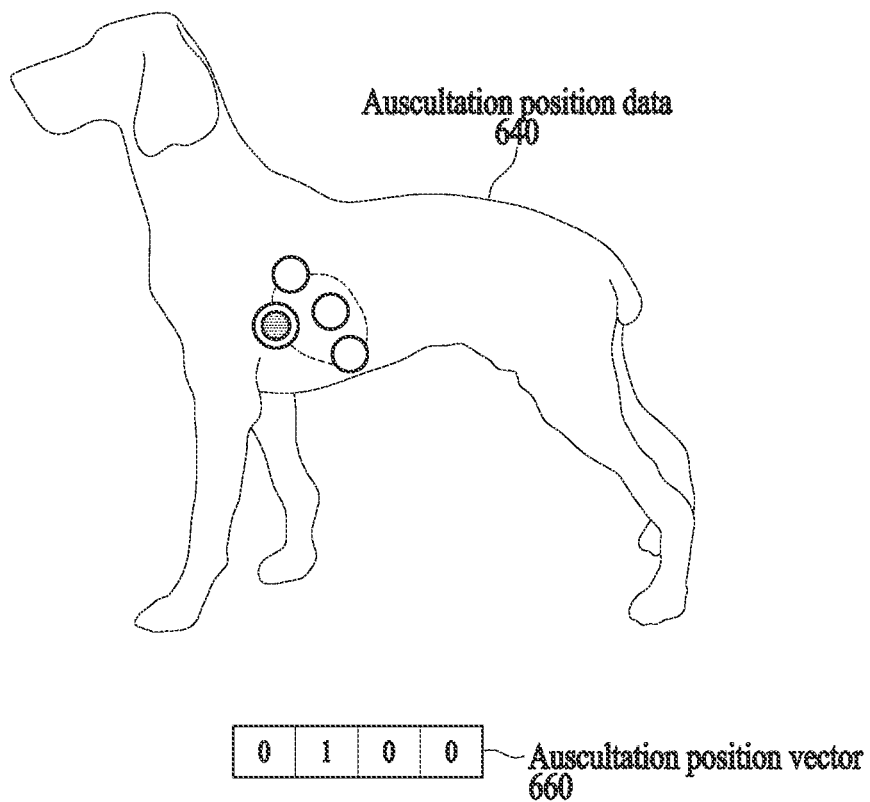

FIGS. 6A and 6B are diagrams for explaining a process of obtaining auscultation position vectors by the electronic apparatus 100 based on auscultation position data according to an example embodiment. Content overlapping descriptions with respect to FIGS. 5A to 5F will be omitted or briefly described.

Referring to FIG. 6A, the electronic apparatus 100 may obtain auscultation position data 600 according to the example embodiment. For example, the electronic apparatus 100 may obtain the auscultation position data 600 including data about a position where the dog's heart sound was measured among positions where heart sound can be auscultated of the dog. Here, positions where heart sound can be auscultated of the dog may include positions P1, P2, P3 and P4, and the auscultation position data 600 may include data about positions where heart sounds are measured among P1 to P4.

According to an example embodiment, the electronic apparatus 100 may identify a position where an auscultation can be performed based on the auscultation position data 600 or setting data. For example, the auscultation position data 600 includes auscultation position data of heart sound of the dog, the electronic apparatus 100 may identify a position where heart sound can be auscultated of the dog as a position where an auscultation can be performed. Alternatively, if the setting data includes a user input by which a dog's heart disease is to be diagnosed, the electronic apparatus 100 may obtain setting data and may identify a position where heart sound can be auscultated of the dog as a position where an auscultation can be performed based on the setting data.

According to an example embodiment, the electronic apparatus 100 may obtain auscultation position vector 620 by embedding the auscultation position data 600. Here, if the number of identified positions where an auscultation can be performed is n, the electronic apparatus 100 may obtain the auscultation position vector 620 of size n. For example, if positions where heart sound can be auscultated of the dog are 4, the electronic apparatus 100 may obtain the auscultation position vector 620 of size 4, and each component of the auscultation position vector 620 may correspond to a position where heart sound can be auscultated of the dog. However, the positions are mere example embodiments, and a position where heart sound can be auscultated of the dog does not limited thereto.

According to an example embodiment, among the components included in the auscultation position vector 620, a component corresponding to the auscultation position may have a first value, and the remaining components may be a second value. For example, if the auscultation position data 600 includes auscultation position data corresponding to P2, among components included in the auscultation position vector 620, a component corresponding to P2 may have a first value, and the remaining components may have a second value. In other words, the auscultation position vector 620 may be expressed as [a second value, a first value, a second value, a second value]. Here, the first value may include 1, and the second value may include 0.

According to an example embodiment, the electronic apparatus 100 may identify an AI model to be used based on the auscultation position data 600 or setting data. For example, if the auscultation position data 600 includes auscultation position data of the dog's heart sound, the electronic apparatus 100 may use an AI model trained based on heart sound data of a dog, auscultation position data of the dog's heart sound and disease data related to the dog's heart. Alternatively, if the setting data includes a user input by which a dog's heart disease is to be diagnosed, the electronic apparatus 100 may use an AI model trained based on the dog's heart sound data, auscultation position data of the dog's heart sound and disease data related to the dog's heart.

Referring to FIG. 6B, the electronic apparatus 100 may obtain auscultation position data 640 according to the example embodiment. For example, the electronic apparatus 100 may obtain the auscultation position data 640 including data indicating that the heart sound was measured at the second position among positions where heart sound can be auscultated of the dog.

According to an example embodiment, the electronic apparatus 100 may identify a position where an auscultation can be performed based on the auscultation position data 640 or setting data. For example, as the auscultation position data 640 includes auscultation position data of the dog's heart sound, the electronic apparatus 100 may identify a position where heart sound can be auscultated of the dog as a position where an auscultation can be performed. Alternatively, as the setting data includes a user input by which diagnosis of the dog's heart disease is to be received, the electronic apparatus 100 may identify a position where heart sound can be auscultated of the dog as a position where an auscultation can be performed.

According to an example embodiment, the electronic apparatus 100 may obtain auscultation position vector 660 by embedding the auscultation position data 640. For example, if it is identified that positions where an auscultation can be performed are 4, the electronic apparatus 100 may obtain the auscultation position vector 660 having values of [0, 1, 0, 0].

Figure 7:
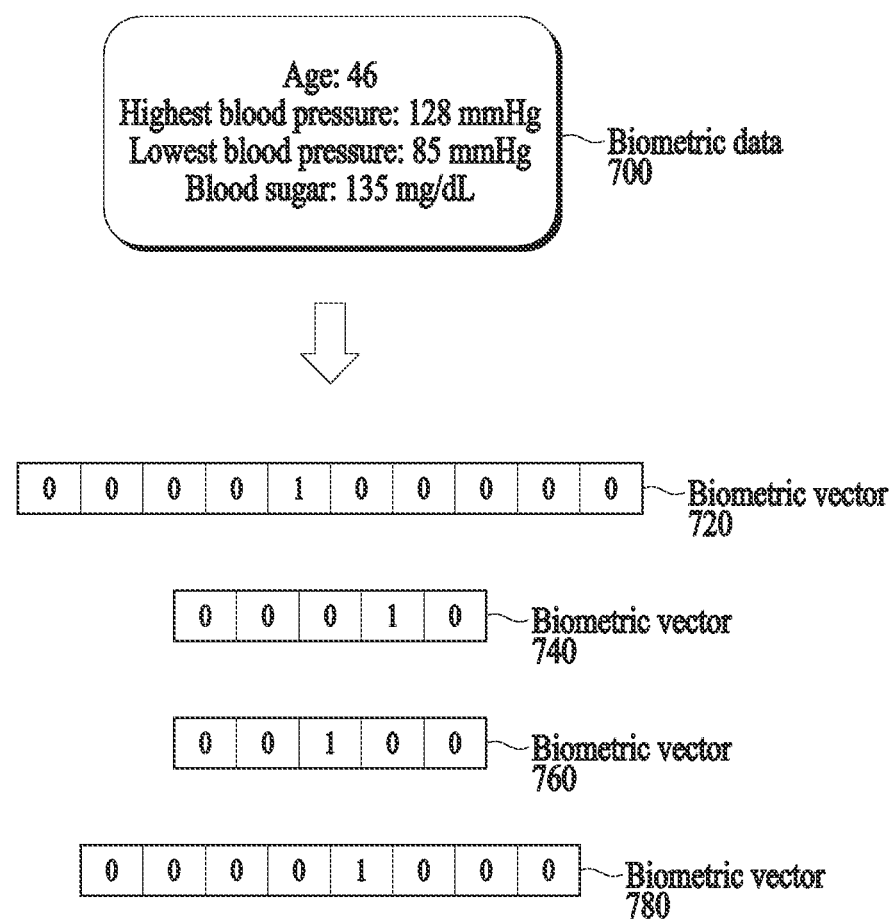
FIG. 7 is a diagram for explaining a process in which an electronic apparatus obtains biometric vectors based on biometric data according to an example embodiment.

FIG. 7 is a diagram for explaining a process in which the electronic apparatus 100 obtains biometric vectors based on biometric data according to an example embodiment.

According to the example embodiment, the electronic apparatus 100 may obtain biometric data 700. For example, the electronic apparatus 100 may obtain the biometric data 700 indicating that a user is 46 years old, has the highest blood pressure of 128 mmHg, the lowest blood pressure of 85 mmHg and a blood sugar of 135 mg/dL.

According to an example embodiment, the electronic apparatus 100 may set the number of categories for embedding the biometric data 700. More specifically, the electronic apparatus 100 may set the number of categories to embed the biometric data 700 as n. Accordingly, the size of the vector embedding the biometric data 700 is n, and each of the n components may correspond to a category of the biometric data 700.

For example, the electronic apparatus 100 may set the number of categories for embedding age data to 10, and set the range of ages included in each category to 10 years old. Accordingly, the size of the vector embedding the age data is 10, and the first component may be from 0 to 9 years old, the second component may be from 10 to 19 years old, . . . , the ninth component may correspond to an age of 80 to 89 years, and the tenth component may correspond to an age of 90 years old or older.

Alternatively, the electronic apparatus 100 may set the number of categories to 5 for embedding the highest blood pressure data, and set the range of highest blood pressure included in each category to 30 mmHg. Accordingly, the size of the vector embedding the highest blood pressure data is 5, and a first component may correspond to a blood pressure of 60 mmHg or less, a second component to 60 mmHg to 90 mmHg, a third component to 90 mmHg to 120 mmHg, a fourth component to 120 mmHg to 150 mmHg, and a fifth component to 150 mmHg or more.

Alternatively, the electronic apparatus 100 may set the number of categories for embedding the lowest blood pressure data to 5, and may set the range of the lowest blood pressure included in each category to 30 mmHg. Accordingly, the size of the vector embedding the lowest blood pressure data is 5, and a first component may correspond to a blood pressure of 30 mmHg or less, a second component to a blood pressure of 30 mmHg to 60 mmHg, a third component to a blood pressure of 60 mmHg to 90 mmHg, a fourth component to a blood pressure of 90 mmHg to 120 mmHg, a fifth component to a blood pressure of 120 mmHg or more.

Alternatively, the electronic apparatus 100 may set the number of categories for embedding blood sugar data to 8, and may set the range of blood sugar included in each category to 20. Accordingly, the size of the vector embedding the blood sugar data is 8, and a first component may correspond to blood sugar of 60 mg/dL or less, a second component to blood sugar of 60 mg/dL to 80 mg/dL, . . . , a seventh component to blood sugar of 160 mg/dL to 180 mg/dL, and an eighth component to blood sugar of 180 mg/dL or higher.

According to an example embodiment, the electronic apparatus 100 may obtain one or more biometric vectors 720, 740, 760 and 780 by embedding the biometric data 700. Here, the size of one or more biometric vectors 720, 740, 760 and 780 may differ according to values that are set for the number of types of biometric data and the number of categories corresponding to each type of biometric data. For example, the electronic apparatus 100 may obtain the biometric vector 720 having values of [0, 0, 0, 0, 1, 0, 0, 0, 0, 0] by embedding age data, and the electronic apparatus 100 may obtain the biometric vector 740 having values of [0, 0, 0, 1, 0] by embedding the highest blood pressure data. Alternatively, the electronic apparatus 100 may obtain the biometric vector 760 having values of [0, 0, 1, 0, 0] by embedding the lowest blood pressure data, and the electronic apparatus 100 may obtain the biometric vector 780 having values of [0, 0, 0, 0, 1, 0, 0, 0] by embedding blood sugar data.

According to an example embodiment, the electronic apparatus 100 may obtain a final biometric vector by concatenating one or more biometric vectors 720, 740, 760 and 780. Accordingly, the sum of values that are set as the number of categories for embedding biometric data according to each type of biometric data may be the size of the final biometric vector. For example, by concatenating one or more biometric vectors 720, 740, 760 and 780, the electronic apparatus 100 may obtain final biometric vectors, having values of [0, 0, 0, 0, 1, 0, 0, 0, 0, 0, 0, 0, 0, 1, 0, 0, 0, 1, 0, 0, 0, 0, 0, 1, 0, 0, 0, 0]. Accordingly, the size of the final biometric vector may be 28, which is the sum of each number of categories for embedding age data, highest blood pressure data, lowest blood pressure data and blood sugar data.

FIGS. 8A to 8F are diagrams for explaining a process in which the electronic apparatus 100 obtains auscultation position maps based on auscultation position data according to an example embodiment. Content overlapping descriptions with respect to FIGS. 5A to 5F will be briefly described or omitted.

Figure 8A:
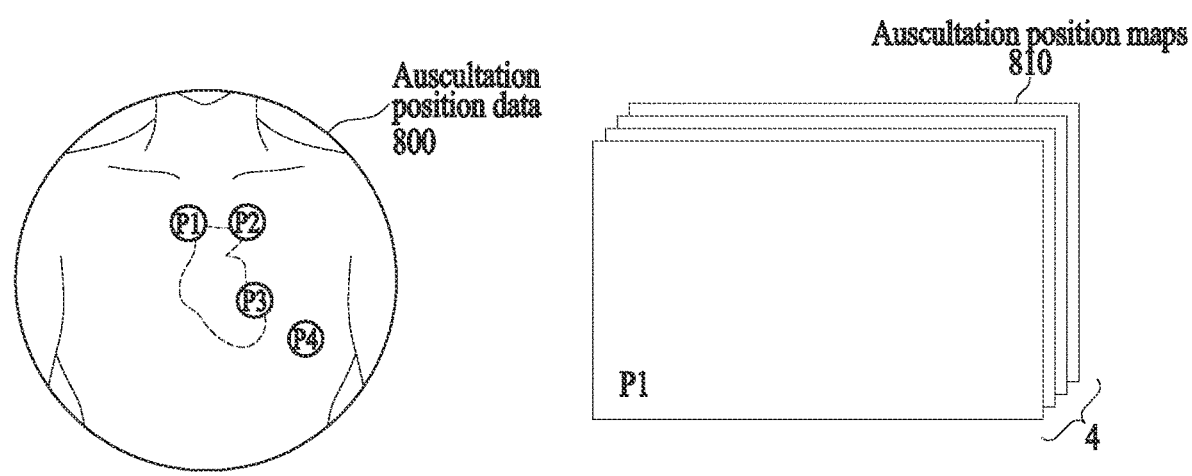
FIGS. 8A to 8F are diagrams for explaining a process in which an electronic apparatus obtains auscultation position maps based on auscultation position data according to an example embodiment.

Referring to FIG. 8A, the electronic apparatus 100 may obtain auscultation position data 800 according to the example embodiment. For example, the electronic apparatus 100 may obtain the auscultation position data 800 including data about the position where the heart sound was measured among positions where heart sound can be auscultated. Here, positions where heart sound can be auscultated may include positions P1, P2, P3 and P4, and the auscultation position data 800 may include data about positions where heart sounds are measured among P1 to P4.

According to an example embodiment, the electronic apparatus 100 may identify a position where an auscultation can be performed based on the auscultation position data 800 or setting data. For example, if the auscultation position data 800 includes auscultation position data of heart sound, the electronic apparatus 100 may identify a position where heart sound can be auscultated as a position where an auscultation can be performed. Alternatively, if the setting data includes a user input by which a heart-related disease is to be diagnosed, the electronic apparatus 100 may obtain setting data, and based on the setting data, the electronic apparatus 100 may identify a position where heart sound can be auscultated as a position where an auscultation can be performed.

According to an example embodiment, the electronic apparatus 100 may obtain auscultation position maps 810 based on the auscultation position data 800. Here, if the number of identified positions where an auscultation can be performed is n, the electronic apparatus 100 may obtain the auscultation position maps 810 including n number of maps. For example, if positions where heart sound can be auscultated are 4, the electronic apparatus 100 may obtain the auscultation position maps 810 including four maps, and each of the four maps may correspond to a position where heart sound can be auscultated.

According to an example embodiment, among the maps included in the auscultation position maps 810, a component of a map corresponding to the auscultation position may have a first value, and the remaining components of the maps may have a second value. For example, if the auscultation position data 800 includes auscultation position data corresponding to P2, among the maps included in the auscultation position maps 810, a component of the map corresponding to P2 may have a first value, and components of the remaining maps may have a second value. Here, the first value may include 1, and the second value may include 0.

According to an example embodiment, the electronic apparatus 100 may identify an AI model to be used based on the auscultation position data 800 or setting data. For example, if the auscultation position data 800 includes auscultation position data of heart sound, the electronic apparatus 100 may use an AI model trained based on heart sound data, auscultation position data of heart sound and heart disease data. Alternatively, if the setting data includes a user input by which a heart-related disease is to be diagnosed, the electronic apparatus 100 may use an AI model trained based on heart sound data, auscultation position data of heart sound and heart disease data.

Figure 8B:
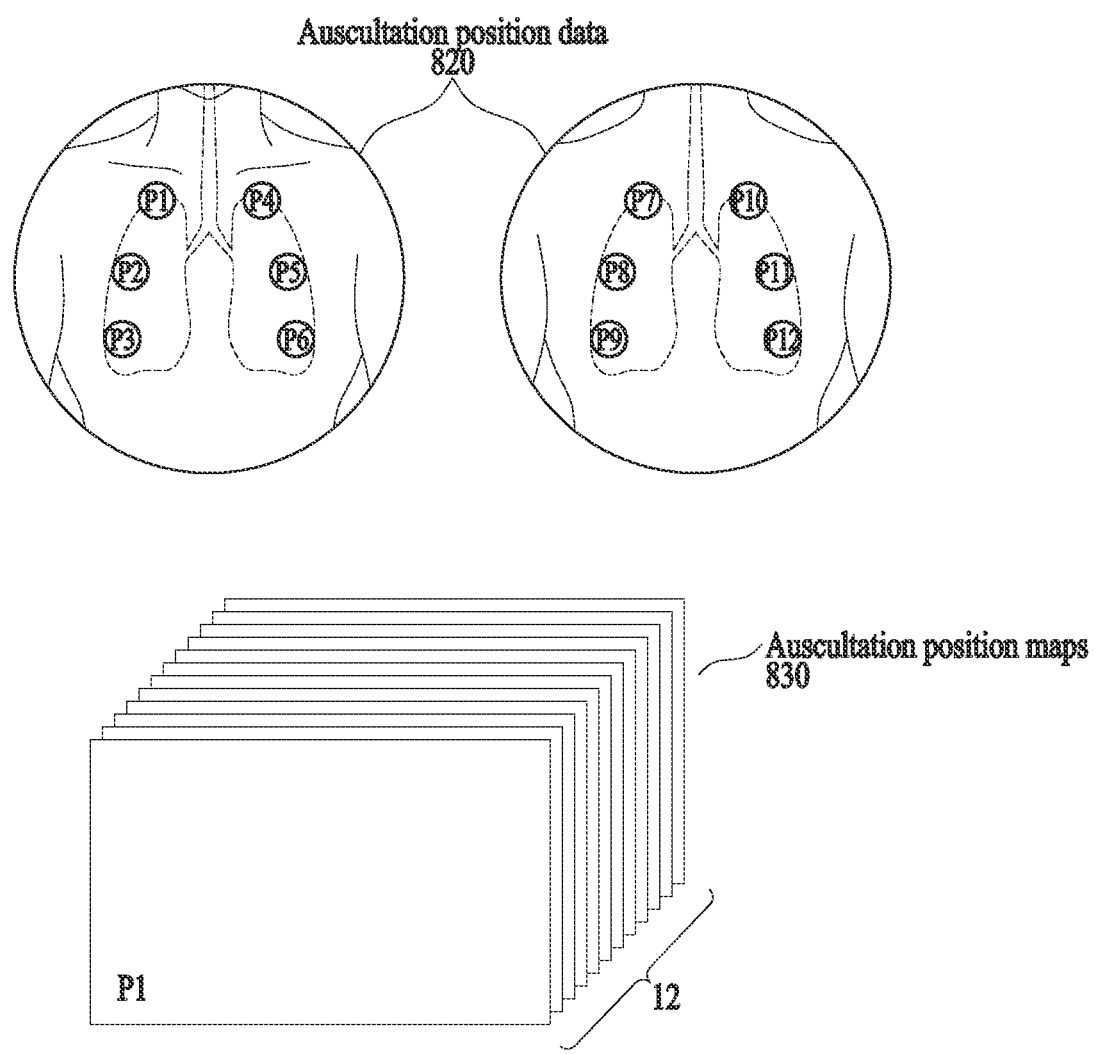

Referring to FIG. 8B, the electronic apparatus 100 may obtain auscultation position data 820 according to the example embodiment. For example, the electronic apparatus 100 may obtain the auscultation position data 820 including data related to a position where lung sound was measured among positions where a lung sound can be auscultated. Here, positions where a lung sound can be auscultated may include positions P1 and P2, and the auscultation position data 820 may include data about positions where lung sounds are measured among positions P1 to P12.

According to an example embodiment, the electronic apparatus 100 may identify a position where an auscultation can be performed based on the auscultation position data 820 and setting data. For example, if the auscultation position data 820 includes auscultation position data of lung sound, the electronic apparatus 100 may identify a position where a lung sound can be auscultated as a position where an auscultation can be performed. Alternatively, if the setting data includes a user input by which a disease related to the lungs is to be diagnosed, the electronic apparatus 100 may obtain the setting data, and may identify a position where a lung sound can be auscultated as a position where an auscultation can be performed based on the setting data.

According to an example embodiment, the electronic apparatus 100 may obtain auscultation position maps 830 based on the auscultation position data 820. Here, if the number of identified positions where an auscultation can be performed is n, the electronic apparatus 100 may obtain the auscultation position maps 830 including n number of maps. For example, if positions where a lung sound can be auscultated are 12, the electronic apparatus 100 may obtain the auscultation position maps 830 including 12 maps, and each of the 12 maps may correspond to a position where a lung sound can be auscultated.

According to an example embodiment, among the maps included in the auscultation position maps 830, a map component corresponding to the auscultation position may have a first value, and the remaining map components may have a second value. For example, if the auscultation position data 820 includes auscultation position data corresponding to P5, among the maps included in the auscultation position maps 830, a component of the map corresponding to P5 may have a first value, and components of the remaining maps may have a second value. Here, the first value may include 1, and the second value may include 0.

According to an example, the electronic apparatus 100 may identify an AI model to be used based on the auscultation position data 820 or setting data. For example, if the auscultation position data 820 includes auscultation position data of lung sound, the electronic apparatus 100 may use an AI model trained based on lung sound data, auscultation position data of lung sound and lung disease data. Alternatively, if the setting data includes a user input by which a disease related to the lungs is to be diagnosed, the electronic apparatus 100 may use an AI model trained based on lung sound data, auscultation position data of lung sound and lung disease data.

Figure 8C:
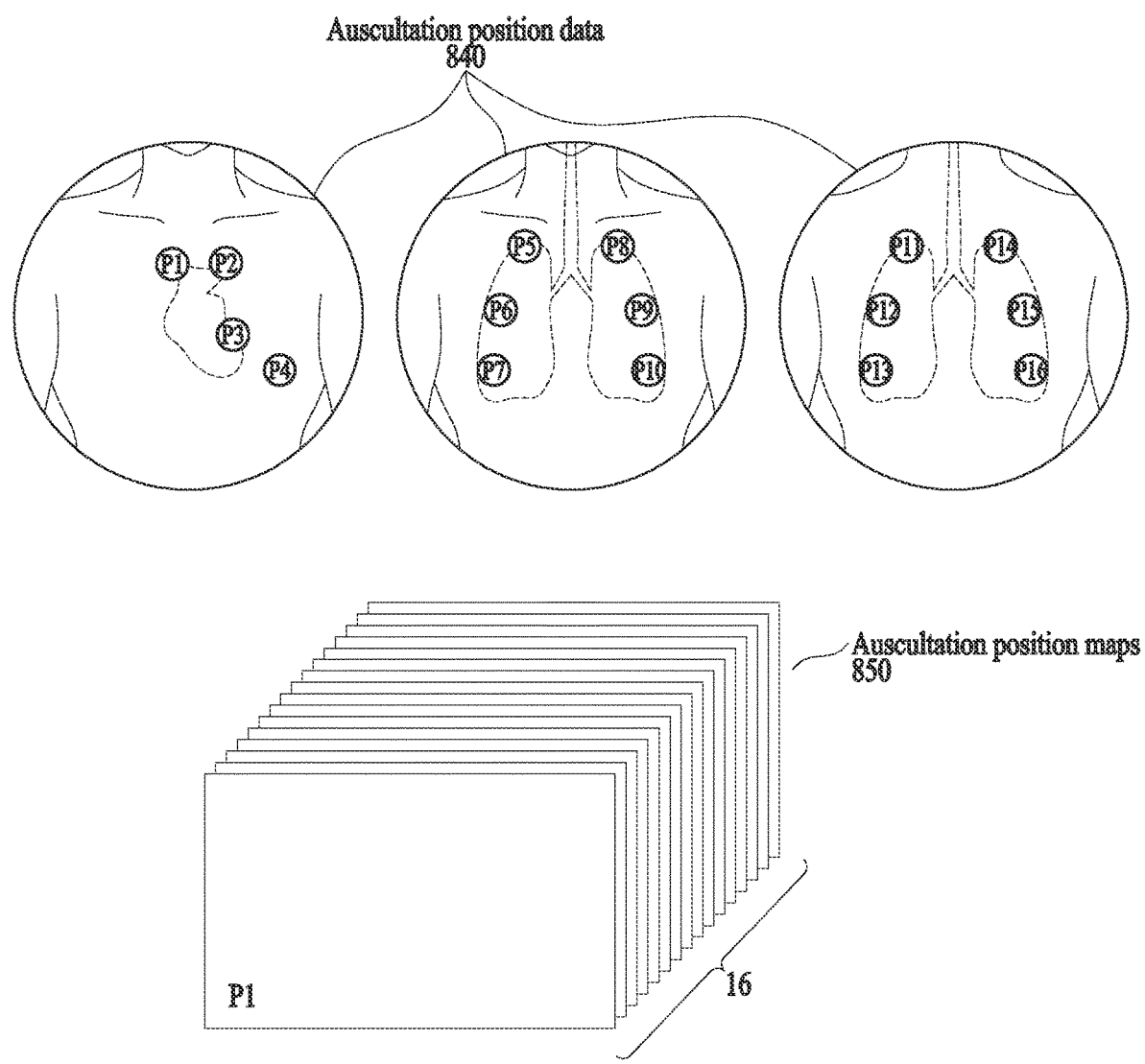

Referring to FIG. 8C, the electronic apparatus 100 may obtain auscultation position data 840 according to the example embodiment. For example, the electronic apparatus 100 may obtain the auscultation position data 840 including data about a position where auscultation sound was measured among positions where a heart sound or a lung sound can be auscultated. Here, positions where heart sound can be auscultated may include positions P1 to P4, positions where a lung sound can be auscultated may include positions P5 to P16, and the auscultation position data 840 may include data about a position where auscultation sound is measured among P1 to P16.

According to an example embodiment, the electronic apparatus 100 may identify a position where an auscultation can be performed based on the auscultation position data 840 or setting. For example, if the auscultation position data 840 includes auscultation position data of heart sound or lung sound, the electronic apparatus 100 may identify a position where a heart sound or a lung sound can be auscultated as a position where an auscultation can be performed. Alternatively, if the setting data does not include a user input on the body part to be diagnosed or includes user inputs by which diseases of all body parts are to be diagnosed, the electronic apparatus 100 may obtain the setting data, and identify a position where a heart sound, a lung sound, or an intestine sound can be auscultated as a position where an auscultation can be performed based on the setting data. However, the positions are mere example embodiments, and a body part that can be identified as a part where an auscultation can be performed is not limited thereto.

According to an example embodiment, the electronic apparatus 100 may obtain auscultation position maps 850 based on the auscultation position data 840. Here, if the number of positions where an auscultation can be performed is n, the electronic apparatus 100 may obtain the auscultation position maps 850 including n number of maps. For example, if positions where heart sound can be auscultated are 4 and positions where a lung sound can be auscultated are 12, the electronic apparatus 100 may obtain the auscultation position maps 850 including 16 maps, and each of the 16 maps may correspond to a position where heart sound can be auscultated.

According to an example embodiment, among the maps included in the auscultation position maps 850, a map component corresponding to the auscultation position may have a first value, and the remaining map components may have a second value. For example, if the auscultation position data 840 includes auscultation position data corresponding to P13, among the maps included in the auscultation position maps 850, a map component corresponding to P13 may have a first value, and the remaining map components may have a second value. Here, the first value may include 1, and the second value may include 0.

According to an example embodiment, the electronic apparatus 100 may identify an AI model to be used based on the auscultation position data 840 or setting data. For example, if the auscultation position data 840 includes auscultation position data of a lung sound, the electronic apparatus 100 may use an AI model trained based on one or more auscultation sound data, one or more auscultation position data and one or more disease data. Alternatively, if the setting data does not include a user input on the body part to be diagnosed or includes user inputs by which diseases of all body parts are to be diagnosed, the electronic apparatus 100 may use an AI model trained based on one or more auscultation sound data, one or more auscultation position data and one or more disease data.

Figure 8D:
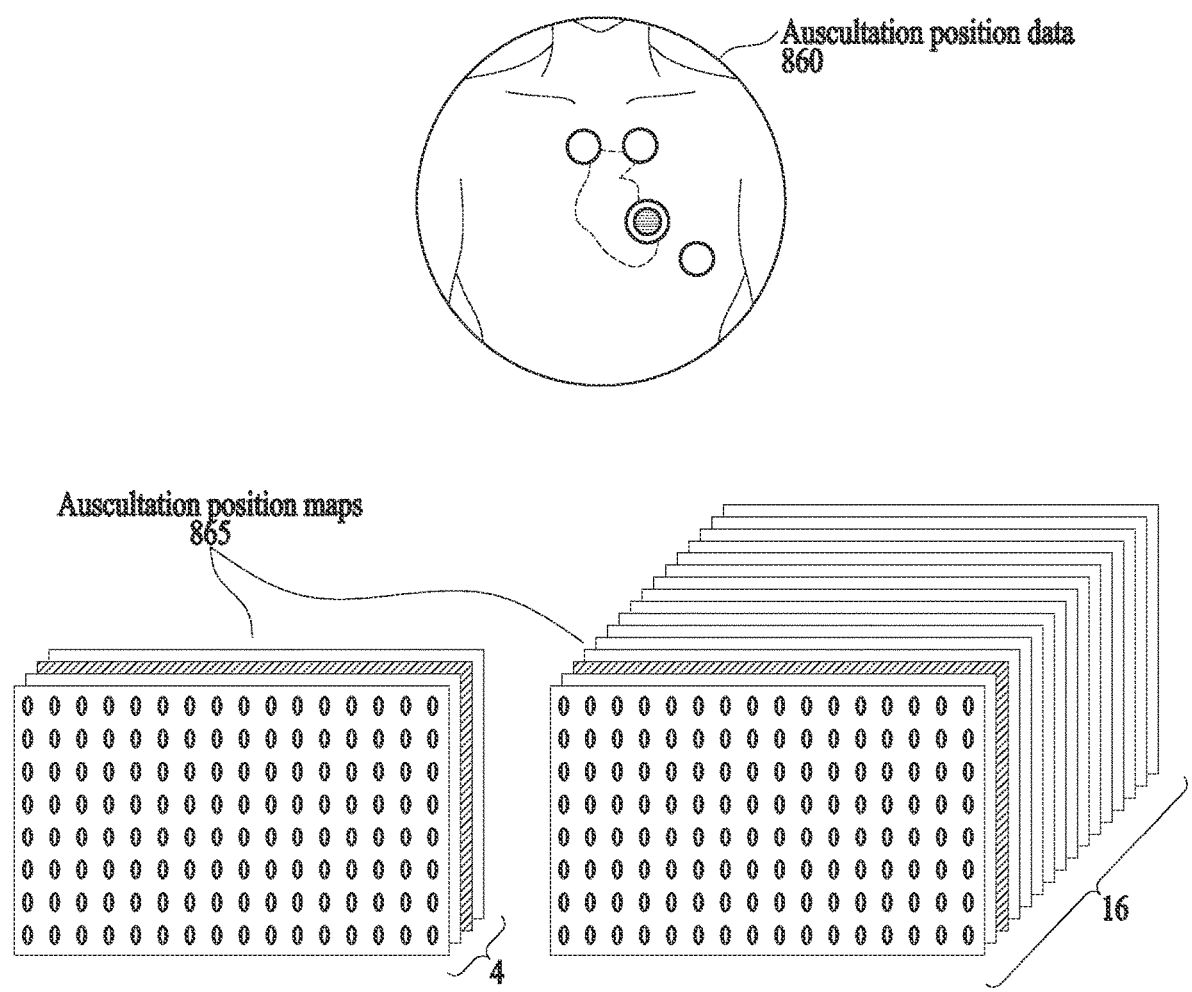

Referring to FIG. 8D, the electronic apparatus 100 may obtain auscultation position data 860 according to the example embodiment. For example, the electronic apparatus 100 may obtain the auscultation position data 860 including data that the heart sound was measured at the third position among positions where heart sound can be auscultated.

According to an example embodiment, the electronic apparatus 100 may identify a position where an auscultation can be performed based on the auscultation position data 860. For example, as the auscultation position data 860 includes auscultation position data of heart sound, the electronic apparatus 100 may identify a position where heart sound can be auscultated as a position where an auscultation can be performed. Alternatively, as the auscultation position data 860 includes auscultation position data of heart sound, the electronic apparatus 100 may identify a position where a heart sound or a lung sound can be auscultated as a position where an auscultation can be performed.

According to an example embodiment, the electronic apparatus 100 may identify a position where an auscultation can be performed based on the setting data. For example, as the setting data includes a user input by which a heart-related disease is to be diagnosed, the electronic apparatus 100 may identify a position where heart sound can be auscultated as a position where an auscultation can be performed based on the setting data. Alternatively, as the setting data does not include a user input regarding a body part for which diagnosis is to be received, or as the setting data includes user inputs by which diseases of all body parts are to be diagnosed, the electronic apparatus 100 may identify a position where a heart sound or a lung sound can be auscultated as a position where an auscultation can be performed based on the setting data.

According to an example embodiment, the electronic apparatus 100 may obtain auscultation position maps 865 based on the auscultation position data 860. For example, if it is identified that positions where an auscultation can be performed are 4, the electronic apparatus 100 may obtain the auscultation position maps 865 including the 4 maps, and a component of a third map among the 4 maps may have a value of 1, and components of the remaining maps may have a value of 0. Alternatively, if it is identified that positions where an auscultation can be performed are 16, the electronic apparatus 100 may obtain the auscultation position maps 865 including 16 maps, and among the 16 maps, a component of a third map may have a value of 1 and components of the remaining maps may have a value of 0.

Figure 8E:
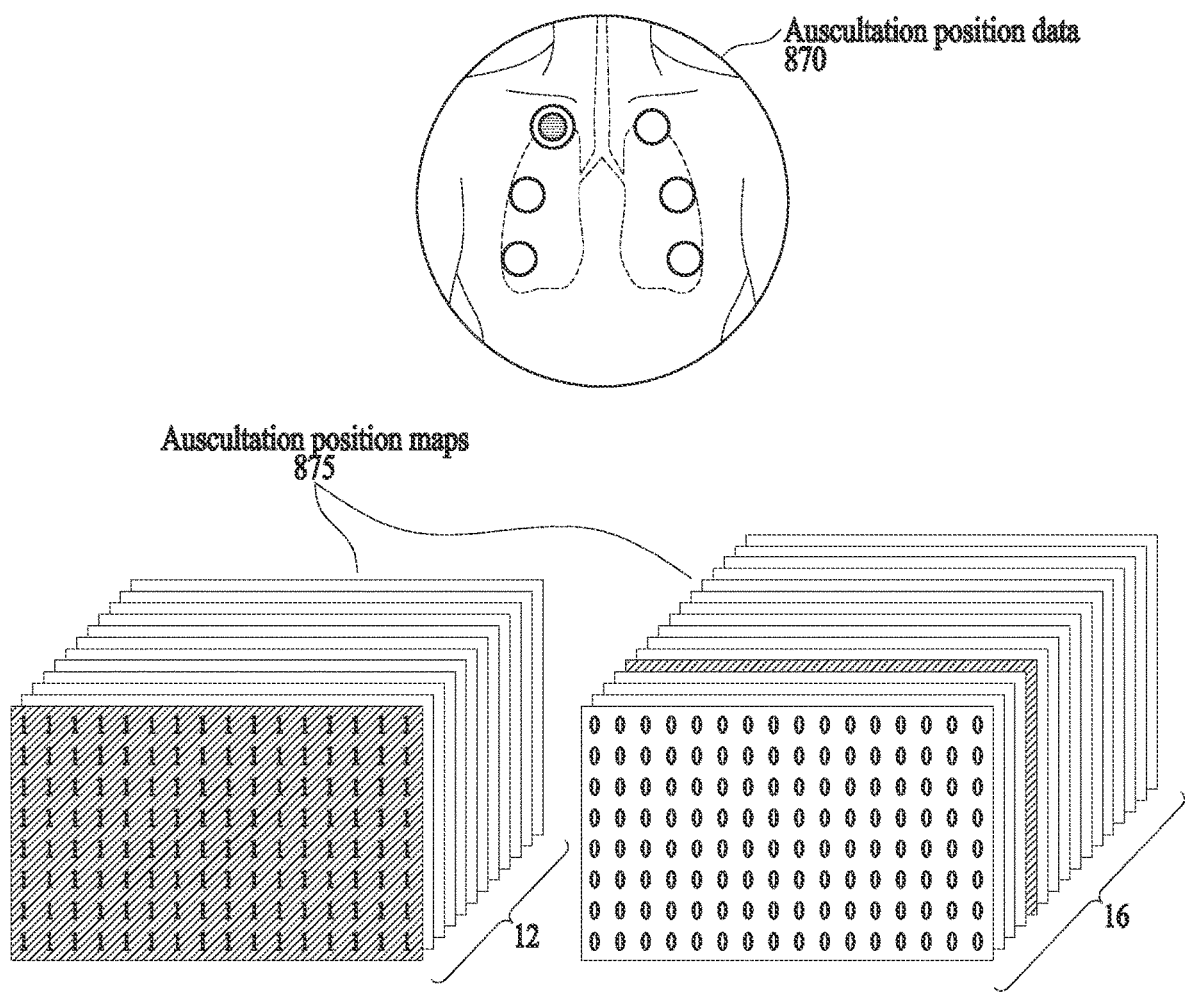

Referring to FIG. 8E, the electronic apparatus 100 may obtain auscultation position data 870 according to the example embodiment. For example, the electronic apparatus 100 may obtain the auscultation position data 870 including data that a lung sound was measured at the first position among positions where a lung sound can be auscultated.

According to an example embodiment, the electronic apparatus 100 may identify a position where an auscultation can be performed based on the auscultation position data 870. For example, as the auscultation position data 870 includes auscultation position data of lung sound, the electronic apparatus 100 may identify a position where a lung sound can be auscultated as a position where an auscultation can be performed. Alternatively, as the auscultation position data 870 includes auscultation position data of lung sound, the electronic apparatus 100 may identify a position where a heart sound or a lung sound can be auscultated as a position where an auscultation can be performed.

According to an example embodiment, the electronic apparatus 100 may identify a position where an auscultation can be performed based on the setting data. For example, as the setting data includes a user input by which diseases of lungs are to be diagnosed, the electronic apparatus 100 may identify a position where a lung sound can be auscultated as a position where an auscultation can be performed based on the setting data. Alternatively, as the setting data does not include a user input regarding a body part for which diagnosis is to be received, or as the setting data includes user inputs by which diseases of all body parts are to be diagnosed, the electronic apparatus 100 may identify a position where a heart sound or a lung sound can be auscultated as a position where an auscultation can be performed based on the setting data.

According to an example embodiment, the electronic apparatus 100 may obtain auscultation position maps 875 based on the auscultation position data 870. For example, if it is identified that positions where an auscultation can be performed are 12, the electronic apparatus 100 may obtain the auscultation position maps 875 including 12 maps, and among the 12 maps, a component of a first map may have a value of 1 and components of the remaining maps may have a value of 0. Alternatively, if it is identified that positions where an auscultation can be performed are 16, the electronic apparatus 100 may obtain the auscultation position maps 875 including 16 maps, and among the 16 maps, a component of a fifth map may have a value of 1 and components of the remaining maps may have a value of 0.

Figure 8F:
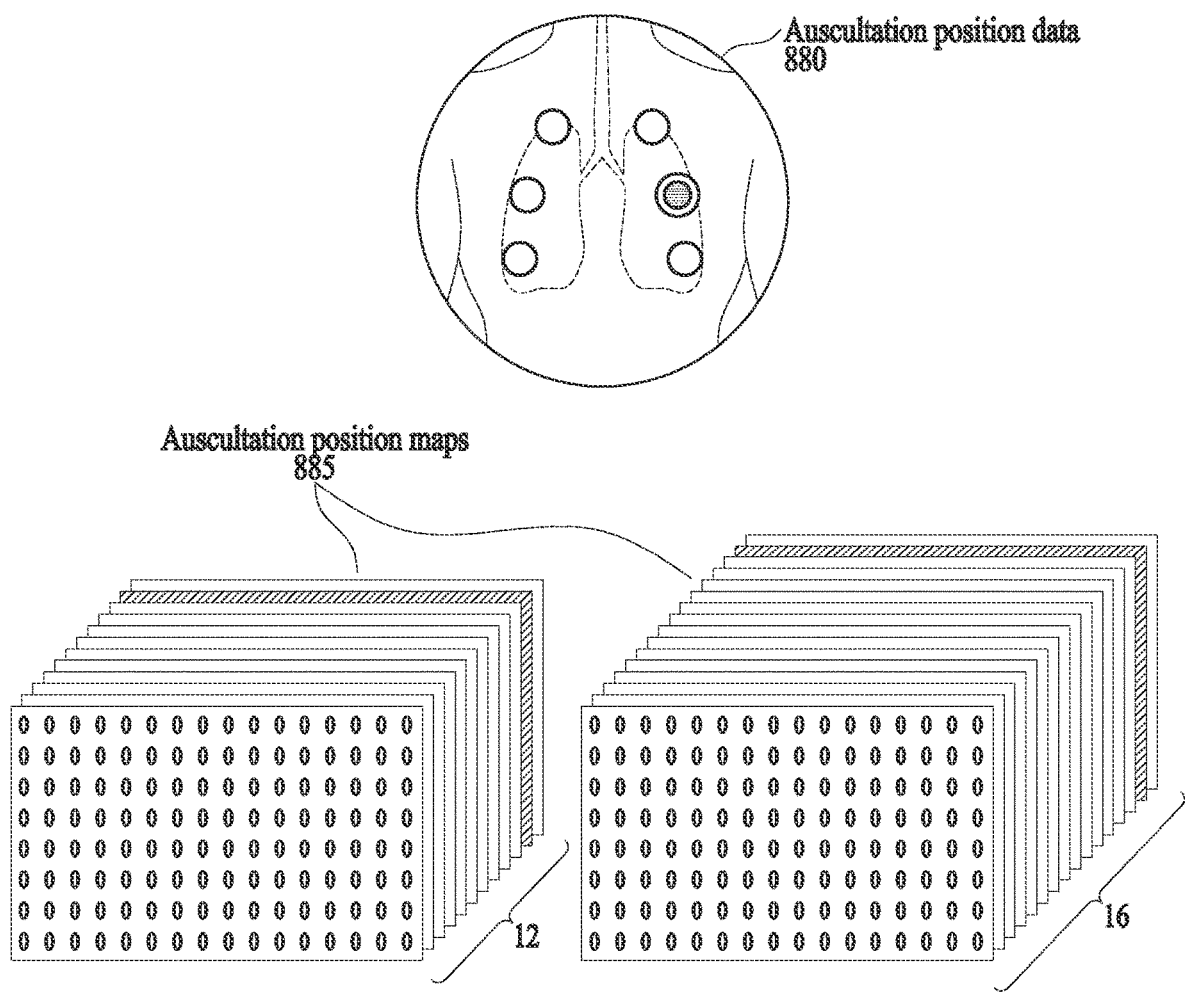

Referring to FIG. 8F, the electronic apparatus 100 may obtain auscultation position data 880 according to the example embodiment. For example, the electronic apparatus 100 may obtain the auscultation position data 880 including data that among positions where a lung sound can be auscultated, the lung sound was measured at the 11th position.

According to an example embodiment, the electronic apparatus 100 may identify a position where an auscultation can be performed based on the auscultation position data 880. For example, as the auscultation position data 880 includes auscultation position data of lung sound, the electronic apparatus 100 may identify a position where a lung sound can be auscultated as a position where an auscultation can be performed. Alternatively, as the auscultation position data 880 includes auscultation position data of lung sound, the electronic apparatus 100 may identify a position where heart sound or lung sound can be auscultated as a position where an auscultation can be performed.

According to an example embodiment, the electronic apparatus 100 may identify a position where an auscultation can be performed based on setting data. For example, as the setting data includes a user input by which diseases of lungs are to be diagnosed, the electronic apparatus 100 may identify a position where a lung sound can be auscultated as a position where an auscultation can be performed based on the setting data. Alternatively, as the setting data does not include a user input regarding a body part for which diagnosis is to be received, or as the setting data includes user inputs by which diseases of all body parts are to be diagnosed, the electronic apparatus 100 may identify a position where a heart sound or a lung sound can be auscultated as a position where an auscultation can be performed based on the setting data.

According to an example embodiment, the electronic apparatus 100 may obtain auscultation position maps 885 based on the auscultation position data 880. For example, if it is identified that positions where an auscultation can be performed are 12, the electronic apparatus 100 may obtain the auscultation position maps 885 including 12 maps, and among the 12 maps, a component of the 11th map may have a value of 1 and components of the remaining maps may have a value of 0. Alternatively, if it is identified that positions where an auscultation can be performed are 16, the electronic apparatus 100 may obtain the auscultation position maps 885 including 16 maps, and among the 16 maps, a component of the 15th map may have a value of 1 and components of the remaining maps may have a value of 0.

Figure 9A:
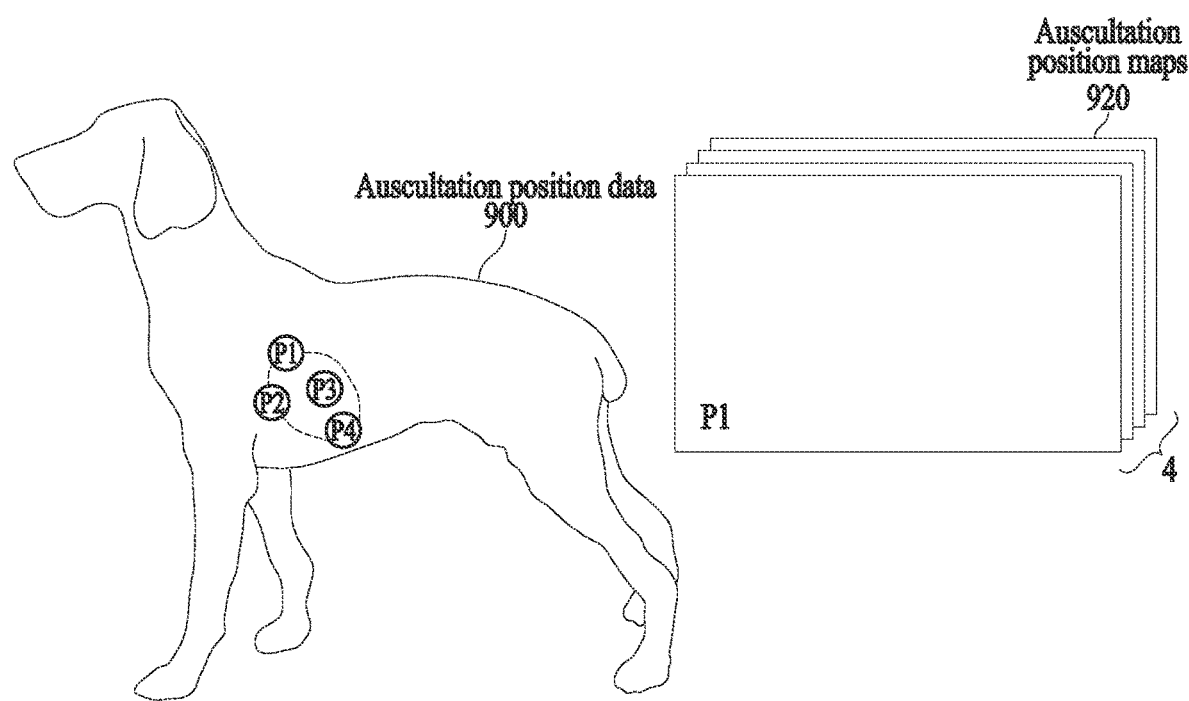
FIGS. 9A and 9B are diagrams for explaining a process in which an electronic apparatus obtains auscultation position maps based on auscultation position data according to an example embodiment.
Figure 9B:
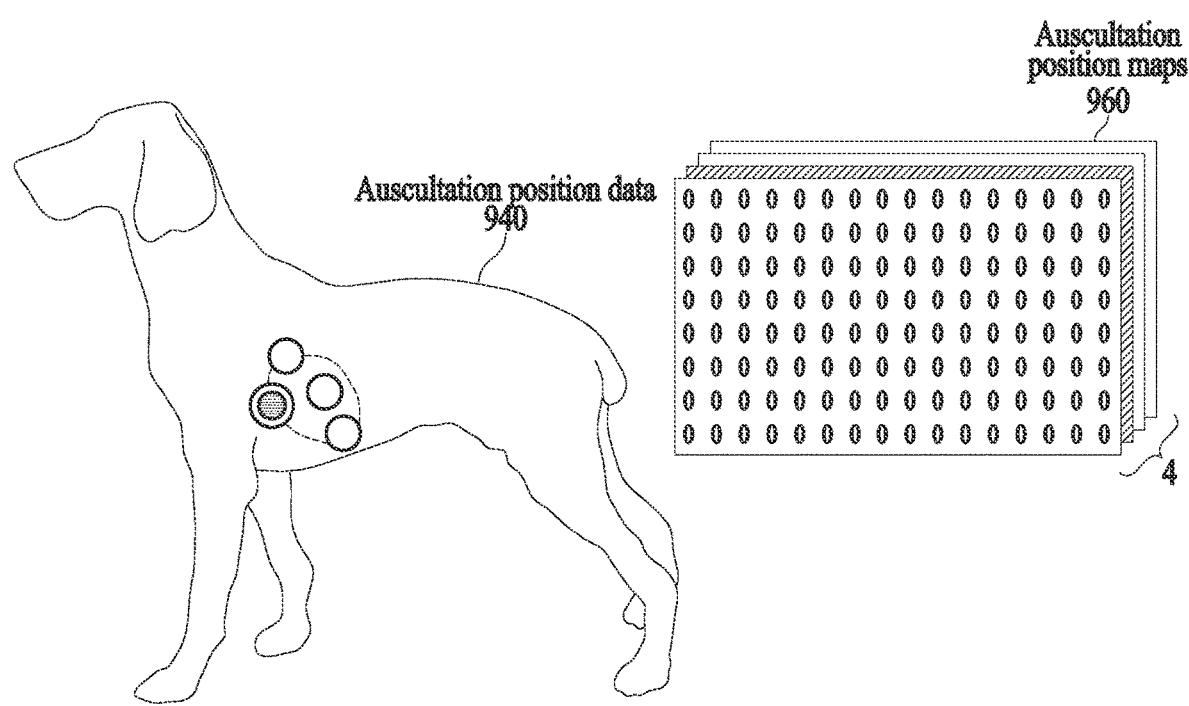

FIGS. 9A and 9B are diagrams for explaining a process in which the electronic apparatus 100 obtains auscultation position maps based on auscultation position data according to an example embodiment. Content overlapping descriptions with respect to FIGS. 8A to 8F will be briefly described or omitted.

Referring to FIG. 9A, the electronic apparatus 100 may obtain auscultation position data 900 according to the example embodiment. For example, the electronic apparatus 100 may obtain the auscultation position data 900 including data related to a position where heart sound of the dog is measured among positions where dog's heart sound can be auscultated. Here, positions where heart sound can be auscultated of the dog may include positions P1, P2, P3 and P4, and the auscultation position data 900 may include data about a position where the heart sound is measured among P1 to P4.

According to an example embodiment, the electronic apparatus 100 may identify a position where an auscultation can be performed based on the auscultation position data 900 or setting data. For example, if the auscultation position data 900 includes auscultation position data of the dog's heart sound, the electronic apparatus 100 may identify a position where heart sound can be auscultated of the dog as a position where an auscultation can be performed. Alternatively, if the setting data includes a user input by which a dog's heart disease is to be diagnosed, the electronic apparatus 100 may obtain setting data and may identify a position where heart sound can be auscultated of the dog as a position where an auscultation can be performed based on the setting data.

According to an example embodiment, the electronic apparatus 100 may obtain auscultation position maps 920 based on the auscultation position data 900. Here, if the number of identified positions where an auscultation can be performed is n, the electronic apparatus 100 may obtain the auscultation position maps 920 including n number of maps. For example, if positions where heart sound can be auscultated of the dog are 4, the electronic apparatus 100 may obtain the auscultation position maps 920 including 4 maps, and each of the 4 maps may correspond to a position where heart sound can be auscultated of the dog. However, the positions are mere example embodiments, and a position where heart sound can be auscultated of the dog is not limited thereto.

According to an example embodiment, among maps included in the auscultation position maps 920, a map component corresponding to the auscultation position may have a first value, and components of the remaining maps may have a second value. For example, if the auscultation position data 900 includes auscultation position data corresponding to position P2, among the maps included in the auscultation position maps 920, a component of the map corresponding to P2 may have a first value, and components of the remaining maps may have a second value. Here, the first value may include 1, and the second value may include 0.

According to an example embodiment, the electronic apparatus 100 may identify an AI model to be used based on the auscultation position data 900 or setting data. For example, if the auscultation position data 900 includes auscultation position data of the dog's heart sound, the electronic apparatus 100 may use an AI model trained based on heart sound data of the dog, auscultation position data of the dog's heart sound and disease data of the dog's heart. Alternatively, if the setting data includes a user input by which a dog's heart disease is to be diagnosed, the electronic apparatus 100 may use an AI model trained based on heart sound data of the dog, auscultation position data of the dog's heart sound and disease data of the dog's heart.

Referring to FIG. 9B, the electronic apparatus 100 may obtain auscultation position data 940 according to the example embodiment. For example, the electronic apparatus 100 may obtain the auscultation position data 940 including data that among positions where heart sound can be auscultated of the dog, the heart sound was measured at the second position.

According to an example embodiment, the electronic apparatus 100 may identify a position where an auscultation can be performed based on the auscultation position data 940 or setting data. For example, as the auscultation position data 940 includes auscultation position data of the dog's heart sound, the electronic apparatus 100 may identify a position where heart sound can be auscultated of the dog as a position where an auscultation can be performed. Alternatively, as the setting data includes a user input by which a disease related to the dog's heart is to be diagnosed, the electronic apparatus 100 may identify a position where heart sound can be auscultated of the dog as a position where an auscultation can be performed.

According to an example embodiment, the electronic apparatus 100 may obtain auscultation position maps 960 based on the auscultation position data 940. For example, if it is identified that positions where an auscultation can be performed are 4, the electronic apparatus 100 may obtain the auscultation position maps 960 including 4 maps, and among the 4 maps, a component of the second map may have a value of 1, and components of the remaining maps may have a value of 0.

FIG. 10 is a diagram for explaining a process in which the electronic apparatus 100 obtains biometric maps based on biometric data according to an example embodiment. Content overlapping descriptions with respect to FIG. 7 will be briefly described or omitted.

According to an example embodiment, the electronic apparatus 100 may obtain biometric data 1000. For example, the electronic apparatus 100 may obtain the biometric data 1000 indicating that the age of a user is 6 years old, the highest blood pressure is 128 mmHg, the lowest blood pressure is 85 mmHg and the blood sugar is 115 mg/dL.

According to an example embodiment, the electronic apparatus 100 may set the number of categories for converting the biometric data 1000 into a map. More specifically, the electronic apparatus 100 may set the number of categories for converting the biometric data 1000 into a map as n. Accordingly, the number of maps included in the maps converted from the biometric data 1000 is n, and each of the n number of maps may correspond to a category of the biometric data 1000.

According to an example embodiment, the electronic apparatus 100 may obtain one or more biometric maps 1020, 1040, 1060 and 1080 based on the biometric data 1000. Here, the number of maps contained in one or more biometric maps 1020, 1040, 1060 and 1080 may be different according to values that are set as the number of types of biometric data and the number of categories corresponding to each type of biometric data. For example, the electronic apparatus 100 may obtain biometric maps 1020 including 10 maps based on the age data, and among the 10 maps, a component of the first map may have a value of 1 and components of the remaining maps may have a value of 0. The electronic apparatus 100 may obtain biometric maps 1040 including 5 maps based on the highest blood pressure data, and among the 5 maps, a component of the fourth map may have a value of 1 and components of the remaining maps may have a value of 0. The electronic apparatus 100 may obtain biometric maps 1060 including 5 maps based on the lowest blood pressure data, and among the 5 maps, a component of the third map may have a value of 1 and components of the remaining maps may have a value of 0. The electronic apparatus 100 may obtain biometric maps 1080 including 8 maps based on blood sugar data, and among the 8 maps, a component of the fourth map may have a value of 1 and components of the remaining maps may have a value of 0.

According to an example embodiment, the electronic apparatus 100 may obtain final biometric maps by combining one or more biometric maps 1020, 1040, 1060 and 1080. Accordingly, the sum of the values that are set as the number of categories for converting the biometric data into a map according to each type of biometric data may be the number of maps included in the final biometric maps. For example, by combining one or more biometric maps 1020, 1040, 1060 and 1080, final biometric maps including 28 maps may be obtained, and among the 28 maps, components of the first map, $14^{th}$ map, $18^{th}$ map and $24^{th}$ map may have a value of 1 and components of the remaining maps may have a value of 0.

Figure 11:
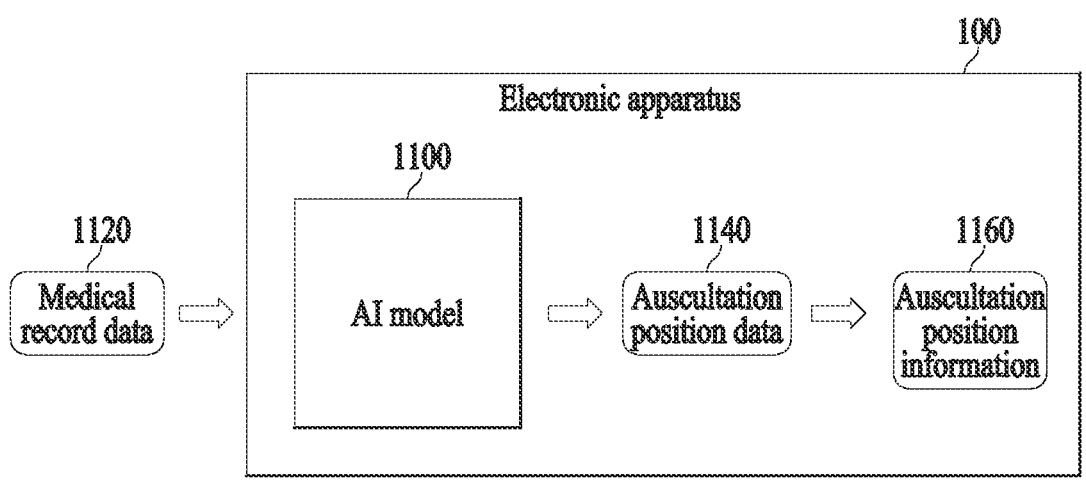
FIG. 11 is a diagram for explaining a process of obtaining auscultation position information by an electronic apparatus based on medical record data according to an example embodiment.

FIG. 11 is a diagram for explaining a process of obtaining auscultation position information by the electronic apparatus 100 based on medical record data according to an example embodiment.

According to an example embodiment, the electronic apparatus 100 may obtain medical record data 1120. For example, a user terminal may obtain a user input for directly entering a medical record, or may receive the medical record data 1120 from an external apparatus, and may transmit the obtained the medical record data 1120 to the electronic apparatus 100. Here, the medical record data may include sentence data described by a medical professional, but it is not limited thereto.

According to an example embodiment, the electronic apparatus 100 may obtain auscultation position data 1140 from the medical record data 1120, using an AI model 1100. More specifically, the electronic apparatus 100 may obtain the auscultation position data 1140 by extracting keywords from the medical record data 1120, using the AI model that extracts keywords. For example, the electronic apparatus 100 may obtain the medical record data 1120 including the sentence "An abnormal sound is heard in the first part of the left side of the front chest." The electronic apparatus 100 may obtain the auscultation position data 1140 by extracting the keywords "front chest," "first part of the left side" from the medical record data 1120.

According to an example embodiment, the electronic apparatus 100 may obtain auscultation position information 1160 based on the auscultation position data 1140. For example, the electronic apparatus 100 may obtain the auscultation position information 1160 from the auscultation position data 1140, using a neural network model such as Word2Vec.

Figure 12A:
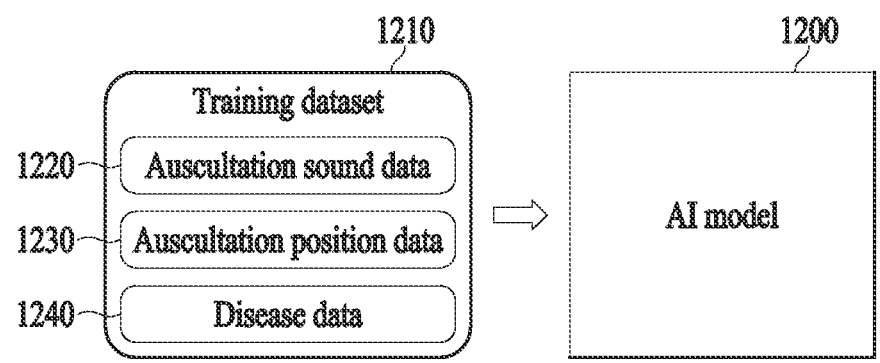
FIGS. 12A to 12C are diagrams for explaining a process of training an AI model by an electronic apparatus according to an example embodiment.
Figure 12B:
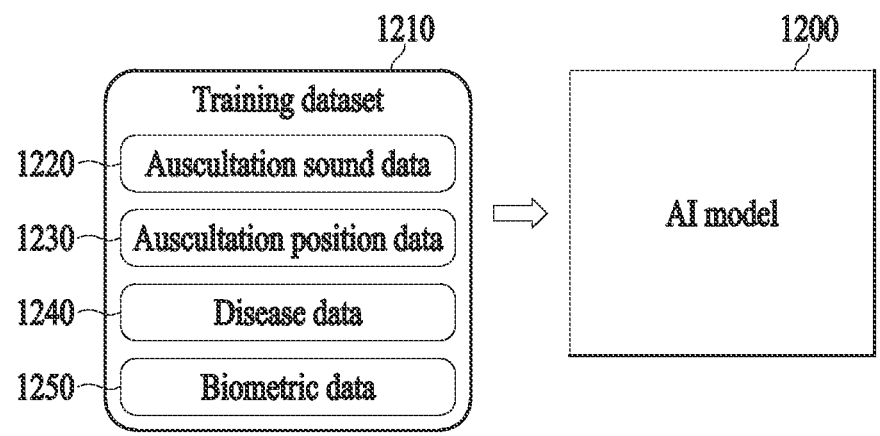
Figure 12C:
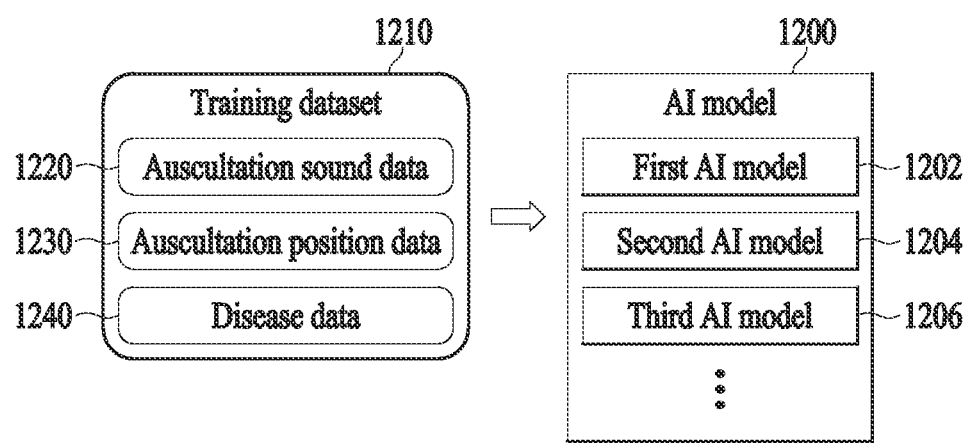

FIGS. 12A to 12C are diagrams for explaining a process of training an AI model by the electronic apparatus 100 according to an example embodiment.

Referring to FIG. 12A, the electronic apparatus 100 may train an AI model 1200 by using a training dataset 1210 including one or more auscultation sound data 1220, one or more auscultation position data 1230 and one or more disease data 1240. Here, each of one or more auscultation sound data 1220, one or more auscultation position data 1230 and one or more disease data 1240 may be paired with corresponding data. For example, the training dataset 1210 may include training data in the form of (auscultation sound data, auscultation position data, disease data).

According to an example embodiment, the training dataset 1210 may include heart-related data. For example, the auscultation sound data 1220 may include data related to clicks, snaps or heart murmurs. The auscultation position data 1230 may include data related to an aortic valve position, a pulmonic valve positon, a tricuspid valve position, or a mitral valve or bicuspid valve position. Further, the disease data 1240 may include data related to AS, aortic insufficiency (AI), mitral stenosis (MS) and mitral valve insufficiency (MVI).

According to an example embodiment, the training dataset 1210 may include lung-related data. For example, the auscultation sound data 1220 may include data related to a vesicular breath sound, a bronchial breath sound, a wheezing sound, a crackling, a pleural friction nub, and rhonchus, and the auscultation position data 1230 may include data on a position where a lung sound can be auscultated. Further, the disease data 1240 may include data related to asthma, chronic obstructive pulmonary disease (COPD), pneumonia, bronchiectasis, interstitial lung disease (ILD) and hydrothorax.

According to an example embodiment, the training dataset 1210 may include data about animals. For example, the auscultation sound data 1220 may include data related to clicks, snapping sound or heart murmur. The auscultation position data 1230 may include data an aortic valve position, a pulmonic valve position, a tricuspid valve position, or a mitral valve or bicuspid valve position. Further, the disease data 1240 may include data related to AS, pulmonic stenosis (PS), patent ductus arteriosus (PDA), MVI, subaortic stenosis (SAS), tricuspid valve insufficiency (TVI) or ventricular septal defect (VDS).

According to an example embodiment, the training dataset 1210 may include auscultation sound data measured from various body parts of a person with a specific disease. For example, the training dataset may include not only training data of (a first auscultation sound, a mitral valve or bicuspid valve position, MS), but also various training data such as (a second auscultation sound, an aortic valve position, MS), (a third auscultation sound, a pulmonic valve position, MS) or (a fourth auscultation sound, a tricuspid valve position, MS). Alternatively, the training dataset may include not only training data of (a first auscultation sound, a first position, pneumonia), but also various trainging data such as (a second auscultation sound, a second position, pneumonia), (a third auscultation sound, a third position, pneumonia) or (a fourth auscultation sound, a fourth position, pneumonia).

As such, as the AI model 1200 is trained based on the auscultation position data 1230 as well as the auscultation sound data 1220, when the auscultation sound data 1220 and the auscultation position data 1230 are input, the electronic apparatus 100 may determine with higher accuracy whether or not the user of the input data has a disease by using the AI model 1200. Further, as the AI model 1200 is trained based on the auscultation sound data 1220 at the optimal position for diagnosing a specific disease, as well as the auscultation sound data 1220 at various positions, even when the auscultation sound data 1220 and the corresponding auscultation position data 1230 at a position other than the optimal positions are input, the electronic apparatus 100 may determine whether the user of the input data has a disease by using the AI model 1200.

Referring to FIG. 12B, the electronic apparatus 100 may train the AI model 1200 by using the training dataset 1210 including one or more auscultation sound data 1220, one or more auscultation position data 1230, one or more disease data 1240 and one or more biometric data 1250. Here, each of one or more auscultation sound data 1220, one or more auscultation position data 1230, one or more disease data 1240 and one or more biometric data 1250 may be paired with corresponding data. For example, the training dataset 1210 may include training data in the form of (auscultation sound data, auscultation position data, disease data, biometric data).

According to an example embodiment, the training dataset 1210 may include auscultation sound data and biometric data measured from various body parts of a person with a specific disease. For example, the training dataset may include various training data such as (a first auscultation sound, a mitral valve or bicuspid valve position, AI, age, body temperature, heart beat regularity), (a second auscultation sound, a tricuspid valve position, AI, age, body temperature, heart beat regularity), (a third auscultation sound, an aortic valve position, AI, age, body temperature, heart beat regularity), and (a fourth auscultation sound, a pulmonic valve position, AI, age, body temperature, heartbeat regularity). Alternatively, the training dataset may include various training data such as (a first auscultation sound, a first position, ILD, age, respiration rate), (a second auscultation sound, a second position, ILD, age, respiration rate), and (a third auscultation sound, a third position, ILD, age, respiration rate).

As such, as the AI model 1200 is trained based on the biometric data 1250 as well as the auscultation sound data 1220 and the auscultation position data 1230, when the auscultation sound data 1220, the auscultation position data 1230 and the biometric data 12500 are input, the electronic apparatus 100 may determine with higher accuracy whether or not the user of the input data has a disease by using the AI model 1200.

Referring to FIG. 12C, the electronic apparatus 100 may train one or more AI models 1202, 1204 and 1206 included in the AI model 1200 by using the training dataset 1210 including one or more auscultation sound data 1220, one or more auscultation position data 1230 and one or more disease data 1240.

For example, the electronic apparatus 100 may train a first AI model 1202 for classifying heart-related diseases, by using a training dataset including one or more heart sound data, one or more auscultation position data of heart sound and one or more heart disease data. Alternatively, the electronic apparatus 100 may train a second AI model 1204 for classifying diseases related to the lungs using a training dataset including one or more lung sound data, one or more auscultation position data of lung sound and one or more lung disease data. The electronic apparatus 100 may train a third AI model 1206 for classifying a dog's heart-related disease, by using a training dataset including one or more dog heart sound data, one or more auscultation position data of dog heart sound and one or more disease data on the dog's heart.

As such, as one or more AI models 1202, 1204 and 1206 included in the AI model 1200 are learned based on different training data according to the body part or species that the user wishes to receive diagnosis, the electronic apparatus 100 may classify diseases with higher accuracy by using the AI model corresponding to the input data.

Figure 13:
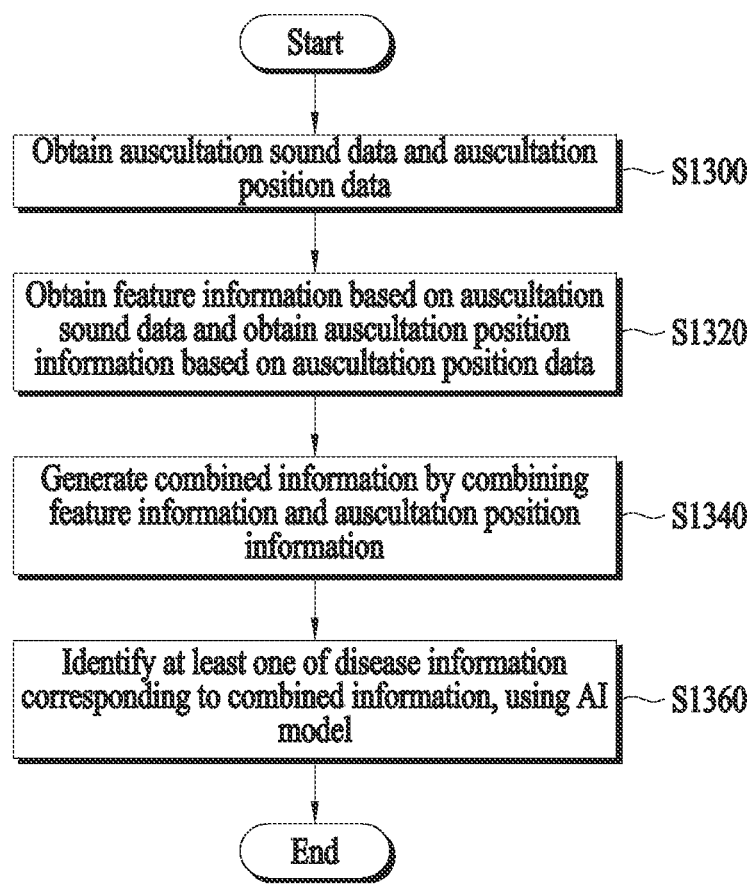
FIG. 13 is a flowchart of a method for classifying diseases using AI of an electronic apparatus according to an example embodiment.

FIG. 13 is a flowchart of a method for classifying diseases using AI of an electronic apparatus according to an example embodiment. For overlapping content, the above description may be applied.

In operation S1300, an electronic apparatus may obtain auscultation sound data and auscultation position data.

According to an example embodiment, the auscultation sound data may include at least one of heart sound data and lung sound data, and the auscultation position data may include data on an auscultation position for heart sound and data on an auscultation position for lung sound.

According to an example embodiment, an electronic apparatus may obtain medical record data when obtaining the auscultation position data, and may obtain the auscultation position data from the medical record data by using an AI model that extracts keywords.

In operation S1320, an electronic apparatus may obtain feature information based on the auscultation sound data, and may obtain auscultation position information based on the auscultation position data.

In operation S1340, an electronic apparatus may generate combined information by combining the feature information and the auscultation position information.

According to an example embodiment, the feature information and the auscultation position information may have a vector form, and when generating the combined information, the electronic apparatus may generate combined information by concatenating the feature information and the auscultation position information. Here, the auscultation position information may include one or more components corresponding to a position where an auscultation can be performed, and among one or more components corresponding to a position where an auscultation can be performed, a component corresponding to the auscultation position may be a first value and the remaining components may have a second value.

According to an example embodiment, the feature information and the auscultation position information may have a form of map, and when generating combined information, the electronic apparatus may generate combined information by adding auscultation position information as a channel to feature information. Here, the auscultation position information may include one or more maps corresponding to positions where an auscultation can be performed, and among one or more maps corresponding to auscultation positions, a map component corresponding to the auscultation position may have a first value and the remaining map components may have a second value.

In operation S1360, the electronic apparatus may identify at least one of disease information corresponding to the combined information, using the AI model.

According to an example embodiment, the electronic apparatus may obtain biometric data, and may obtain biometric information based on the biometric data. Here, the combined information may be further combined with the biometric information, and the biometric data may include at least one of heart beat regularity data, respiration rate data, respiratory regularity data, body temperature data, age data, blood pressure data and blood sugar data.

For example, the electronic apparatus may obtain the biometric data, and may obtain vector-type biometric information based on the biometric data. Here, the biometric information may include one or more components corresponding to a set number of categories, and among one or more components corresponding to the set number of categories, a component corresponding to a category including a value of the biometric data may have a first value and the remaining components may have a second value.

Alternatively, an electronic apparatus may obtain biometric data, and may obtain biometric information in the form of a map based on the biometric data. Here, the biometric information may include one or more components corresponding to the set number of categories, and among one or more maps corresponding to the set number of categories, a component of the map corresponding to a category including a value of the biometric data may have a first value and the remaining map components may have a second value.

According to an example embodiment, auscultation sound data may include heart sound data, and the AI model may include a first AI model for classifying for heart-related disease. Alternatively, when obtaining feature information, the electronic apparatus may remove a frequency domain other than a frequency in which a heart sound exists in the auscultation sound data, and when identifying at least one of disease information, the electronic apparatus may identify at least one of disease information about the heart corresponding to the combined information by using the first AI model.

According to an example embodiment, the auscultation sound data may include lung sound data, and the AI model may include a second AI model for classifying lung-related disease. Alternatively, when obtaining feature information, the electronic apparatus may remove a frequency domain other than a frequency in which lung sounds exists in the auscultation sound data, and when identifying at least one of disease information, the electronic apparatus may identify at least one of disease information about the lung corresponding to the combined information by using the second AI model.

According to an example embodiment, the AI model may be trained based on a training dataset including one or more auscultation sound data, one or more auscultation position data and one or more disease data. Here, the training dataset may further include one or more biometric data.

According to an example embodiment, the AI model may include the first AI model for classifying heart-related diseases and the second AI model for classifying lung-related diseases. The first AI model may be trained based on a training dataset including one or more heart sound data, one or more auscultation position data of heart sound and one or more heart disease data. The second AI model may be trained based on a training dataset including one or more lung sound data, one or more auscultation position data of lung sound and one or more lung disease data.

Figure 14:
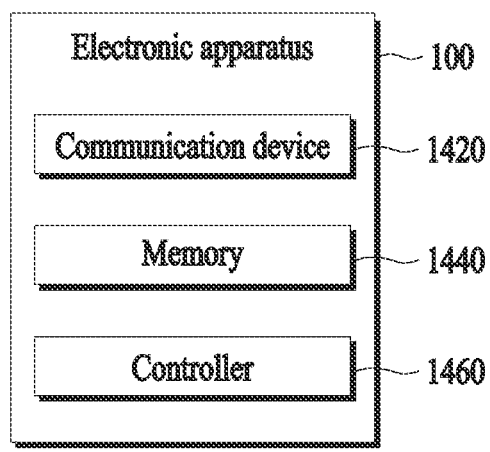
FIG. 14 is a block diagram of an electronic apparatus according to an example embodiment.

FIG. 14 is a block diagram of the electronic apparatus 100 according to an example embodiment.

The electronic apparatus 100 may include a communication device 1420, a memory 1440 and a controller 1460 according to the example embodiment. In the electronic apparatus 100 illustrated in FIG. 14, only elements related to the example embodiments are illustrated. Therefore, those skilled in the art can understand that other general-purpose elements may be further included in addition to the elements illustrated in FIG. 14. Since the electronic apparatus 100 may include information related to the server described above, descriptions of overlapping contents are omitted. In an example embodiment, the communication apparatus may include one or more transceivers. Further, in an example embodiment, the controller may include one or more processors.

The communication device 1420 is an apparatus for performing wired/wireless communication and can communicate with an external electronic apparatus. An external electronic apparatus may be a terminal or a server. Further, communication technologies used by the communication device 1420 include global system for mobile communication (GSM), code division multi access (CDMA), long term evolution (LTE), 5G, wireless LAN (WLAN), wireless-fidelity (Wi-Fi), Bluetooth™, radio frequency identification (RFID), Infrared Data Association (IrDA), ZigBee and near field communication (NFC).

The controller 1460 may control overall operations of the electronic apparatus 100 and process data and signals. The controller 1460 may be composed of at least one hardware unit. Further, the controller 1460 may operate by one or more software modules generated by executing program codes stored in the memory 1440. Since the controller 1460 may include a processor and a memory, the processor may execute program codes stored in the memory to control overall operations of the electronic apparatus 100 and process data and signals. Further, in an example embodiment, the controller 1460 may include at least one processor.

The controller 1460 may obtain auscultation sound data and auscultation position data, may obtain feature information based on the auscultation sound data, may obtain auscultation position information based on the auscultation position data, may generate combined information by combining the feature information and the auscultation position information, and may identify at least one of disease information corresponding to the combined information by using the AI model.

The electronic apparatus according to the above-described example embodiments may include a processor, a memory for storing and executing program data, a permanent storage such as a disk drive, and/or a user interface apparatus such as a communication port, a touch panel, a key and/or a button that communicates with an external apparatus. Methods implemented as software modules or algorithms may be stored in a computer-readable recording medium as computer-readable codes or program instructions executable on the processor. Here, the computer-readable recording medium includes a magnetic storage medium (for example, ROMs, RAMs, floppy disks and hard disks) and an optically readable medium (for example, CD-ROMs and DVDs). The computer-readable recording medium may be distributed among network-connected computer systems, so that the computer-readable codes may be stored and executed in a distributed manner. The medium may be readable by a computer, stored in a memory, and executed on a processor.

The example embodiments may be represented by functional block elements and various processing steps. The functional blocks may be implemented in any number of hardware and/or software configurations that perform specific functions. For example, an example embodiment may adopt integrated circuit configurations, such as memory, processing, logic and/or look-up table, that may execute various functions by the control of one or more microprocessors or other control apparatuses. Similar to that elements may be implemented as software programming or software elements, the example embodiments may be implemented in a programming or scripting language such as C, C++, Java, assembler, etc., including various algorithms implemented as a combination of data structures, processes, routines, or other programming constructs. Functional aspects may be implemented in an algorithm running on one or more processors. Further, the example embodiments may adopt the existing art for electronic environment setting, signal processing, and/or data processing. Terms such as "mechanism," "element," "means" and "configuration" may be used broadly and are not limited to mechanical and physical elements. The terms may include the meaning of a series of routines of software in association with a processor or the like.

The above-described example embodiments are merely examples, and other embodiments may be implemented within the scope of the claims to be described later.

What is claimed is:

1. A method, performed by an electronic apparatus, for classifying heart and lung related diseases using artificial intelligence (AI), the method comprising:
    obtaining auscultation sound data, auscultation position data and setting data including information regarding body part;
    obtaining feature information based on the auscultation sound data and obtaining auscultation position information based on the auscultation position data;
    generating combined information by combining the feature information and the auscultation position information; and
    identifying at least one of heart and lung related disease information corresponding to the combined information, by inputting the combined information to an AI model,
    wherein the feature information, the auscultation position information and the combined information have a vector form,
    wherein the obtaining of the auscultation position information comprises obtaining the auscultation position information by embedding the auscultation position data,
    wherein the generating of the combined information comprises generating the combined information by concatenating the feature information and the auscultation position information,
    wherein the auscultation position information includes configured number of components corresponding to possible auscultation positions,
    wherein, from among the configured number of components corresponding to the possible auscultation positions, a component corresponding to the auscultation position has a first value and other remaining components have a second value, and
    wherein the configured number is determined based on the information regarding body part.

2. The method of claim 1, further comprising:
    obtaining biometric data; and
    obtaining biometric information based on the biometric data,
    wherein the combined information is further combined with the biometric information.

3. The method of claim 2, wherein the biometric data includes at least one of heart beat regularity data, respiration rate data, respiratory regularity data, body temperature data, age data, blood pressure data, and blood sugar data.

4. The method of claim 1, further comprising:
    obtaining biometric data; and
    obtaining biometric information in a vector form based on the biometric data, wherein the combined information is further concatenated with the biometric information.

5. The method of claim 4,
wherein the biometric information includes one or more components corresponding to a set number of categories, and
wherein, from among the one or more components corresponding to the set number of categories, a component corresponding to a category including a value of the biometric data has a first value and other remaining components have a second value.

6. The method of claim 1,
wherein the feature information and the auscultation position information have a form of a map, and
wherein the generating the combined information comprises generating the combined information by adding the auscultation position information as a channel to the feature information.

7. The method of claim 6,
wherein the auscultation position information includes one or more maps corresponding to possible auscultation positions, and
wherein, from among the one or more maps corresponding to the possible auscultation positions, a component of a map corresponding to the auscultation position has a first value and components of other remaining maps have a second value.

8. The method of claim 6, further comprising:
obtaining biometric data; and
obtaining biometric information in a form of a map based on the biometric data,
wherein the biometric information is further added to the combined information as a channel.

9. The method of claim 8,
wherein the biometric information includes one or more maps corresponding to a set number of categories, and
wherein, from among the one or more maps corresponding to the set number of categories, a component of a map corresponding to a category including a value of the biometric data has a first value and components of other remaining maps have a second value.

10. The method of claim 1,
wherein the auscultation sound data includes at least one of heart sound data and lung sound data, and
wherein the auscultation position data includes data related to an auscultation position for a heart sound and data related to an auscultation position for a lung sound.

11. The method of claim 1,
wherein the auscultation sound data includes heart sound data,
wherein the AI model includes a first AI model for classifying heart-related diseases,
wherein the obtaining the feature information comprises removing a frequency domain other than a frequency domain in which a heart sound is present from the auscultation sound data, and
wherein the identifying at least one of heart-related disease information comprises identifying at least one of heart-related disease information about a heart corresponding to the combined information, by inputting the combined information to the first AI model.

12. The method of claim 1, wherein the auscultation sound data includes lung sound data,
wherein the AI model includes a second AI model for classifying lung-related diseases,
wherein the obtaining the feature information comprises removing a frequency domain other than a frequency domain in which a lung sound is present from the auscultation sound data, and
wherein the identifying at least one of lung-related disease information comprises identifying at least one of lung-related disease information about a lung corresponding to the combined information, by inputting the combined information to the second AI model.

13. The method of claim 1, wherein the obtaining the auscultation position data comprises:
obtaining medical record data; and
obtaining the auscultation position data from the medical record data using an AI model that extracts a keyword.

14. The method of claim 1, wherein the AI model is trained based on a training dataset including one or more auscultation sound data, one or more auscultation position data and one or more disease data.

15. The method of claim 14, wherein the training dataset further includes one or more biometric data.

16. The method of claim 1,
wherein the AI model includes a first AI model for classifying heart-related diseases and a second AI model for classifying lung-related diseases,
wherein the first AI model is trained based on a training dataset including one or more heart sound data, one or more auscultation position data of heart sound and one or more heart-related disease data, and
wherein the second AI model is trained based on a training dataset including one or more lung sound data, one or more auscultation position data of lung sound and one or more lung-related disease data.

17. A computer-readable non-transitory recording medium having a program for executing the method of claim 1 on a computer.

18. An electronic apparatus, comprising:
a communication device;
a memory; and
a controller,
wherein the controller is configured to:
obtain auscultation sound data, auscultation position data and setting data including information regarding body part,
obtain feature information based on the auscultation sound data and obtaining auscultation position information based on the auscultation position data,
generate combined information by combining the feature information and the auscultation position information,
identify at least one of heart and lung related disease information corresponding to the combined information, by inputting the combined information to an AI model,
wherein the feature information, the auscultation position information and the combined information have a vector form,
wherein the obtaining of the auscultation position information comprises obtaining the auscultation position information by embedding the auscultation position data,
wherein the generating of the combined information comprises generating the combined information by concatenating the feature information and the auscultation position information,
wherein the auscultation position information includes configured number of components corresponding to possible auscultation positions,
wherein, from among the configured number of components corresponding to the possible auscultation positions, a component corresponding to the auscultation position has a first value and other remaining components have a second value, and wherein the configured number is determined based on the information regarding body part.

* * * * *